(12) United States Patent
Gianchandani et al.

(10) Patent No.: US 8,212,552 B2
(45) Date of Patent: Jul. 3, 2012

(54) WIRELESS BILIARY STENT SYSTEM WITH WISHBONE-ARRAY RESONANT MAGNETOELASTIC SENSOR AND CONFORMAL MAGNETIC LAYER

(75) Inventors: Yogesh B. Gianchandani, Ann Arbor, MI (US); Scott Green, Davison, MI (US); Mark Thomas Richardson, St. Joseph, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 415 days.

(21) Appl. No.: 12/476,218

(22) Filed: Jun. 1, 2009

(65) Prior Publication Data

US 2009/0295383 A1 Dec. 3, 2009

Related U.S. Application Data

(60) Provisional application No. 61/057,778, filed on May 30, 2008.

(51) Int. Cl.
*G01R 33/12* (2006.01)
*A61F 2/82* (2006.01)
*A61N 2/00* (2006.01)
(52) U.S. Cl. .......................... 324/228; 600/12; 623/1.15
(58) Field of Classification Search .................. 324/228; 600/12; 623/1.15
See application file for complete search history.

(56) References Cited

U.S. PATENT DOCUMENTS

| | | | | |
|---|---|---|---|---|
| 4,907,462 A | * | 3/1990 | Obama et al. | ............ 73/862.335 |
| 6,416,540 B1 | | 7/2002 | Mathur | |
| 7,860,567 B2 | * | 12/2010 | Belalcazar et al. | ............. 607/17 |
| 2002/0133219 A1 | * | 9/2002 | Barry | ............................ 623/1.15 |
| 2002/0188207 A1 | * | 12/2002 | Richter | .......................... 600/486 |
| 2005/0267569 A1 | * | 12/2005 | Barrett et al. | ................ 623/1.44 |
| 2006/0140867 A1 | * | 6/2006 | Helfer et al. | ................. 424/9.32 |
| 2011/0004109 A1 | * | 1/2011 | Stahmann | ..................... 600/486 |

OTHER PUBLICATIONS

Donnelli, et al., "Plastic Biliary Stent Occlusion: Factors Involved and Possible Preventive Approaches," Clinical Medicine & Research, vol. 5, No. 1, pp. 53-60 (2007).

(Continued)

*Primary Examiner* — Bot Ledynh
(74) *Attorney, Agent, or Firm* — Marshall, Gerstein & Borun LLP

(57) ABSTRACT

A stent and a magnetoelastic resonant sensor are provided for sensor a physical characteristic in a bodily vessel or cavity. External coils interact with the sensor to induce a resonance that is responsive to the physical characteristic, such that the device may wirelessly measure physical characteristics such as mass loading effects and viscosity changes due to progression of pathology in implanted stents and stent grafts. The sensor may be fashioned from a magnetoelastic material and may be integrated near the inner sidewall of the stent. The sensor may take on a complex patterned shape to enhance the sensitivity and flexibility of the sensor structure. When the sensor is interrogated with a time-varying magnetic field, the sensor will mechanically vibrate and generate a magnetic flux which is maximum at a resonant characteristic determined by the mass load on the sensor and the viscosity of the fluid surrounding the sensor. By correlating the measured resonant characteristic to the mass load and viscosity, the pathological state in and around the stent can be determined.

49 Claims, 20 Drawing Sheets

OTHER PUBLICATIONS

Green, et al., "Photochemically Patterned Biliary Stents with Integrated Permanent Magnets and Deformable Assembly Features for Wireless Magnetoelastic Tissue Growth Sensing," Transducers pp. 213-217 (2007).

Lin, et al., "Embrittlement of Amorphous Fe40Ni38Mo4B18 Alloy by Electrolytic Hydrogen," Met. and Mat. Trans. A, vol. 26, No. 1, pp. 197-201 (1995).

Lagorce, et al, "Magnetic and Mechanical Properties of Micromachined Strontium Ferrite/Polyimide Composites," JMEMS, vol. 6, No. 4, pp. 307-312 (1997).

Green, et al. "Wireless Magnetoelastic Monitoring of Biliary Stents," Journal of Microelectromechanical Systems, 18(1):64-78 (2009).

* cited by examiner

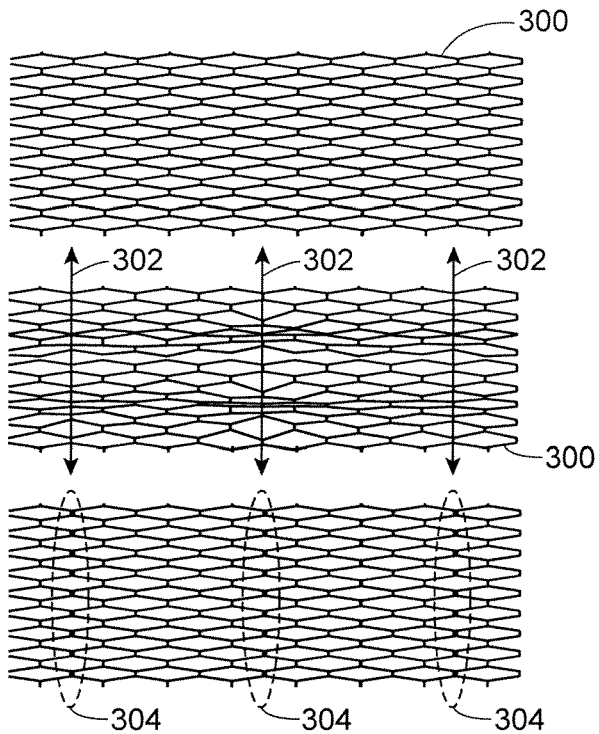
*FIG. 7A*
*FIG. 7B*
*FIG. 7C*
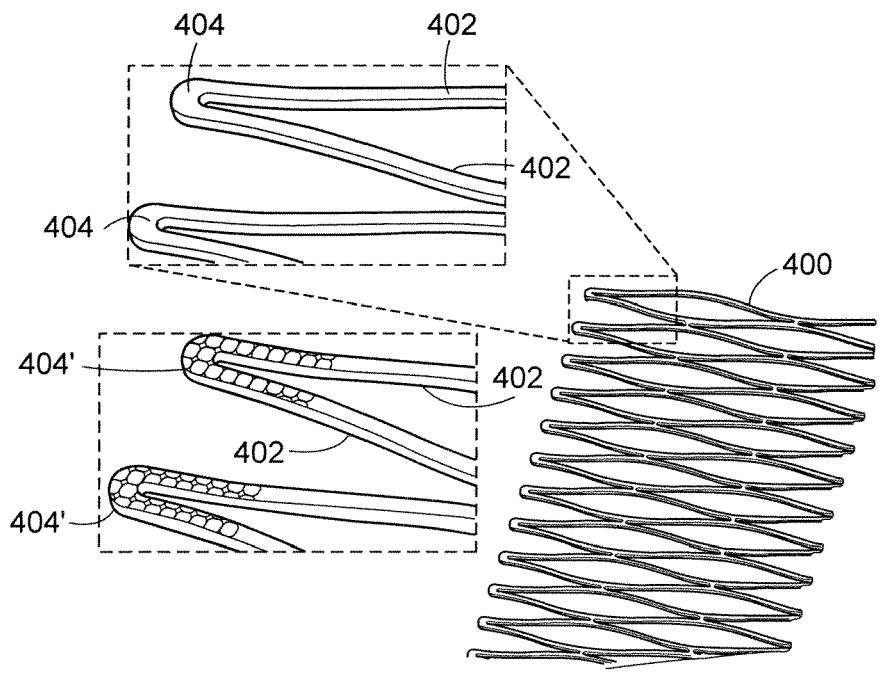
*FIG. 8*

WIRELESS BILIARY STENT SYSTEM WITH WISHBONE-ARRAY RESONANT MAGNETOELASTIC SENSOR AND CONFORMAL MAGNETIC LAYER

CROSS REFERENCE TO RELATED APPLICATIONS

This application claims the benefit of U.S. Provisional Application No. 61/057,778, filed May 30, 2008, the entirety of which is expressly incorporated herein by reference.

SPONSORED RESEARCH

This invention was made with government support under grants EEC0744962and EEC9986866 awarded by the National Science Foundation. The government has certain rights in the invention.

BACKGROUND OF THE DISCLOSURE

1. Field of the Disclosure

The disclosure relates generally to systems for measuring physical characteristics of a bodily vessel, and more particularly to surgically embedded magnetoelastic sensors for measuring physical characteristics.

2. Brief Description of Related Technology

Stents are typically mesh tubular structures that impart and maintain patency in a variety of vessels and ducts that have become constricted as a result of stenotic pathology. Although the act of implanting a stent relieves symptoms caused by the constriction, in-stent restenosis, i.e., the reappearance of cavity narrowing, typically due to the reaction of the body to the presence of the stent, is a risk associated with all stenting procedures.

An example of a stent application area is the bile duct, which transports bile between the liver, gall bladder, pancreas, and small intestine. The constriction relieved by stent implantation is often due to pancreatitis, cholangitis, tumors, or gallstones. Restenosis can occur in an average of 4-5 months via formation of a bacterial matrix known as biliary "sludge." See, e.g., G. Donnelli, et al., "Plastic Biliary Stent Occlusion: Factors Involved and Possible Preventive Approaches," Clinical Medicine & Research, Vol. 5, No. 1, 2007, pp. 53-60.

The timeframe for clinically significant restenosis to occur varies from case to case. Current techniques for diagnosing a blockage are indirect and rely on detecting enzyme levels that may not increase until after the blockage is significant. The combined effect of the unknown pathogenesis time course and the indirect testing methods can result in either unnecessary, prescheduled interventions or in untimely interventions after patients exhibit outward symptoms of the blockage (and liver damage has already occurred). As such, a direct method of diagnosis would enable timely intervention and eliminate unnecessary procedures.

SUMMARY OF THE DISCLOSURE

Techniques have been developed for magnetoelastic wireless sensing of sludge accumulation utilizing externally applied AC interrogative and stent-integrated DC biasing magnetic fields. See, S. R. Green, et al., "Photochemically Patterned Biliary Stents with Integrated Permanent Magnets and Deformable Assembly Features for Wireless Magnetoelastic Tissue Growth Sensing," Transducers 2007, June 2007, pp. 213-217, which is incorporated herein by reference in its entirety. In such techniques, magnetic fields cause a magnetoelastic sensor integrated with the stent to resonate at a frequency that changes as local viscosity increases and as sludge accumulates. The resulting mechanical resonance generates a time-varying magnetic field that can be measured with an external pick-up coil. Once measured, an external system could identify the viscosity changes and determine when a likely in-stent restenosis has occurred. In these techniques, the magnetoelastic sensor was a ribbon sensor with discrete neodymium magnets (e.g., rectangular strips) placed on the stent to optimally bias the anisotropy of that ribbon sensor.

In comparison, components that conform to or mimic the open, flexible structure of the stent would lead to a system that is better able to withstand and accommodate the deformations required during catheter-based delivery, as well as lead to a system that preserves the structural functionality of the stent. Therefore, the present application describes an integrated magnetoelastic system with a sensor and biasing permanent magnet layer that in some examples conforms to the meshed topology and tubular curvature of a biliary stent. The device can be modified for desired operation by adjusting the structural patterning, sensor shaping, and sensor materials used.

A system in accordance with same examples may contain a stent, a magnetoelastic resonant sensor, a magnetized layer for biasing the sensor, and external coils and circuitry for interacting with the resonant sensor. The stent, sensor, and biasing layer are all intended for implantation and preferably are integrated together. The system is intended to wirelessly measure physical characteristics such as mass loading effects and viscosity changes due to progression of pathology in implanted stents and stent grafts (e.g. in-stent restenosis in cardiovascular stents, sludge accumulation and bile viscosity changes in biliary stents, encrustation in ureteral stents, thrombosis formation in aortic abdominal aneurysm stent grafts, etc.). The stent or stent graft may be formed of a composition that includes plastic or metal and is generally tubular and may have a mesh-like structure. The sensor may be fashioned from a magnetoelastic material (such as amorphous metals or rare-earth giant magnetostrictive materials) and is integrated near the inner sidewall of the stent. The patterned structure of the sensor may contain any of these materials or compositions thereof, i.e., polymers, plastics, metals, or magnetoelastic materials such as amorphous metals or rare-earth giant magnetostrictive materials. The sensor may take on a simple ribbon, strip, ring, or disc geometry, but more preferably the sensor is patterned in a more complex shape to enhance the sensitivity and flexibility of the sensor structure. That pattern may be a mesh pattern of repeating, interconnected cells, such as a wishbone-array pattern, a zigzag pattern, hexagonal pattern, etc. In many applications, flexibility is important to ensure deliverability and placement of the stent/sensor combination in tortuous anatomy.

When the sensor is interrogated with a time-varying magnetic field, the sensor will mechanically vibrate and generate a magnetic flux. The sensor response will be maximal at a resonant characteristic that is determined by the mass load on the sensor and the viscosity of the fluid surrounding the sensor. By correlating the measured resonant characteristic to the mass load and viscosity, the pathological state in and around the stent can be determined. The magnetized layer may provide a uniform and steady ("direct current") magnetic field with a fixed orientation with respect to the sensor. This field biases the sensor for optimal response. The system may also be realized by applying the steady magnetic field with external (not implanted) components. The external coils couple to the sensor by generating magnetic fields and picking up the resulting magnetic flux from the sensor. The circuitry drives and measures the external coils to determine the resonant characteristic of the sensor. This resonant characteristic may be a resonant frequency, an anti-resonant frequency, the bandwidth between these two frequencies, or the quality factor of either the anti-resonant or the resonant peak.

The more complex, patterned sensor offers some advantages over typical ribbon sensors. First, the fine feature sizes and large open area of the patterned nature of the sensor presents little obstruction to bile flow, which is the primary objective of a biliary stent. Second, the sensors are much more accommodating of the large deformations required for catheter-based delivery. Third, the sensors have a higher sensitivity to viscosity changes, which is a clinically relevant parameter in many pathological conditions. The physical pathology characteristic may be an accumulated mass (such as accumulated sludge in a bile duct) or viscosity or other measurable trait of fluid/mass in a vessel and correlative to vibrational energy generated in a magnetoelastic sensor element.

In an example, a magnetoelastic sensor for use in measuring a physical pathology characteristic within an implanted stent, the sensor comprises an elongated body with a patterned structure, formed of a magnetoelastic material, and positioned within the stent such that the sensor will mechanically vibrate under application of a time-varying magnetic field and generate a magnetic flux that has a resonant characteristic that varies with a value of the physical pathology characteristic within the implanted stent.

In another example, an apparatus comprises a stent having a tubular structure when deployed; and a sensor inserted within the stent and having an elongated body having a patterned structure and formed of a magnetoelastic material to mechanically vibrate under application of a time-varying magnetic field to generate a magnetic flux having a resonant characteristic that varies with a value of a physical pathology characteristic within the implanted stent, wherein the stent has a conformal magnetic layer for imparting a biasing magnetic field on the sensor.

In another example, a method of measuring a physical pathology characteristic within an implantable stent comprises: disposing a sensor within the stent, the sensor comprising an elongated body having a patterned structure formed of a magnetoelastic material to mechanically vibrate under the application of a magnetic field to generate a magnetic flux having a resonant characteristic that varies with a value of the physical pathology characteristic within the implanted stent; applying an externally generated stimulation magnetic field to at least a first region of the sensor, the stimulation magnetic field being a time-varying magnetic field; and in response to the externally generated stimulation magnetic field and at least at a second region of the sensor, generating a transmitting magnetic field that varies with the value of the physical pathology characteristic.

BRIEF DESCRIPTION OF THE DRAWING FIGURES

For a more complete understanding of the disclosure, reference should be made to the following detailed description and accompanying drawing figures, in which like reference numerals identify like elements in the figures, and in which:

FIGS. 7A-7C illustrate a uniform magnetoelastic sensor (FIG. 7A), anti-nodal points for the sensor (FIG. 7B), and the magnetoelastic sensor with increased sensitivity to a pathology characteristic at the anti-nodal points (FIG. 7C);

FIG. 8 illustrates a magnetoelastic sensor having textured surfaces at various locations;

DETAILED DESCRIPTION OF PREFERRED EMBODIMENTS

Metal biliary stents generally reach their final in situ diameter via an elastic self-expansion. This is in opposition to the plastic expansion of typical balloon-assisted cardiac stents. The need for large elastic diameter recovery in biliary stents leads to not only the utilization of materials with superior elastic properties (e.g. chrome-nickel Elgiloy or nickel-titanium Nitinol) but also to the use of open diamond-shaped patterns. Often these patterns are formed by braiding filaments into a tubular shape.

Described herein are techniques in which a magnetoelastic sensor is designed mimicking the design of the accompanying stent. That is, sensors may be designed to use materials with superior elastic properties and in which those materials are shaped into patterned structures like that of stents, e.g., patterned mesh structures. In some examples, wishbone shaped patterns having diamond-shaped openings throughout have been proposed.

Figure 1:
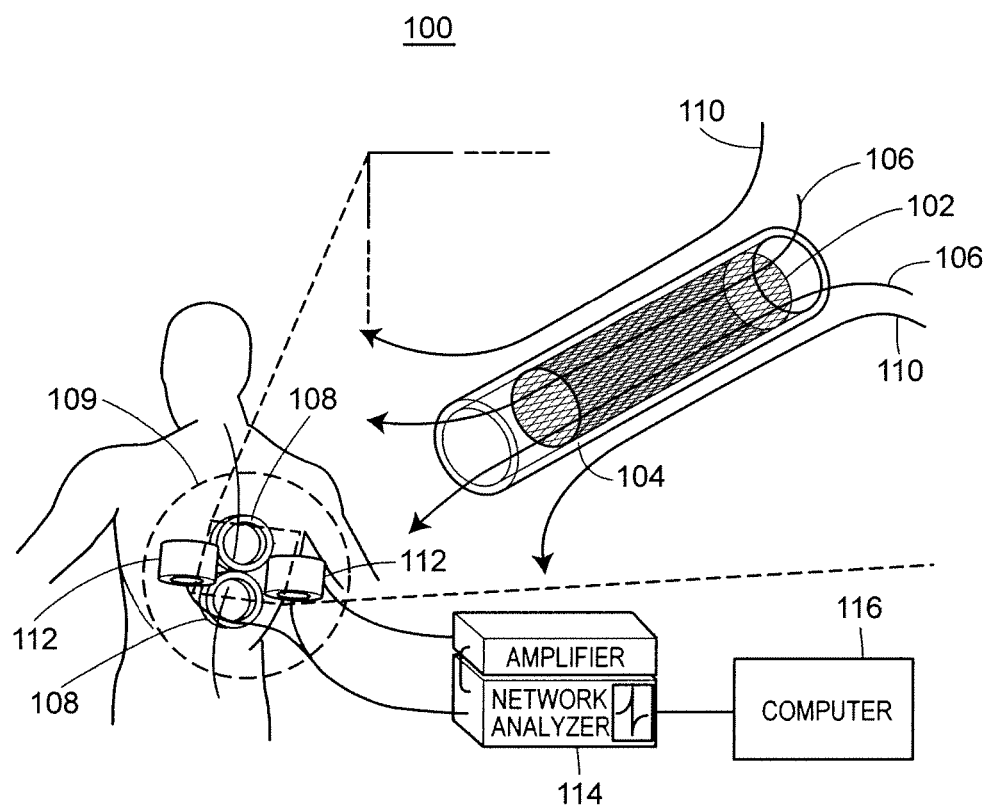
FIG. 1 illustrates a system for sensing sludge accumulation or other biliary physical characteristics using a magnetoelastic sensing mechanism.
Figure 16:
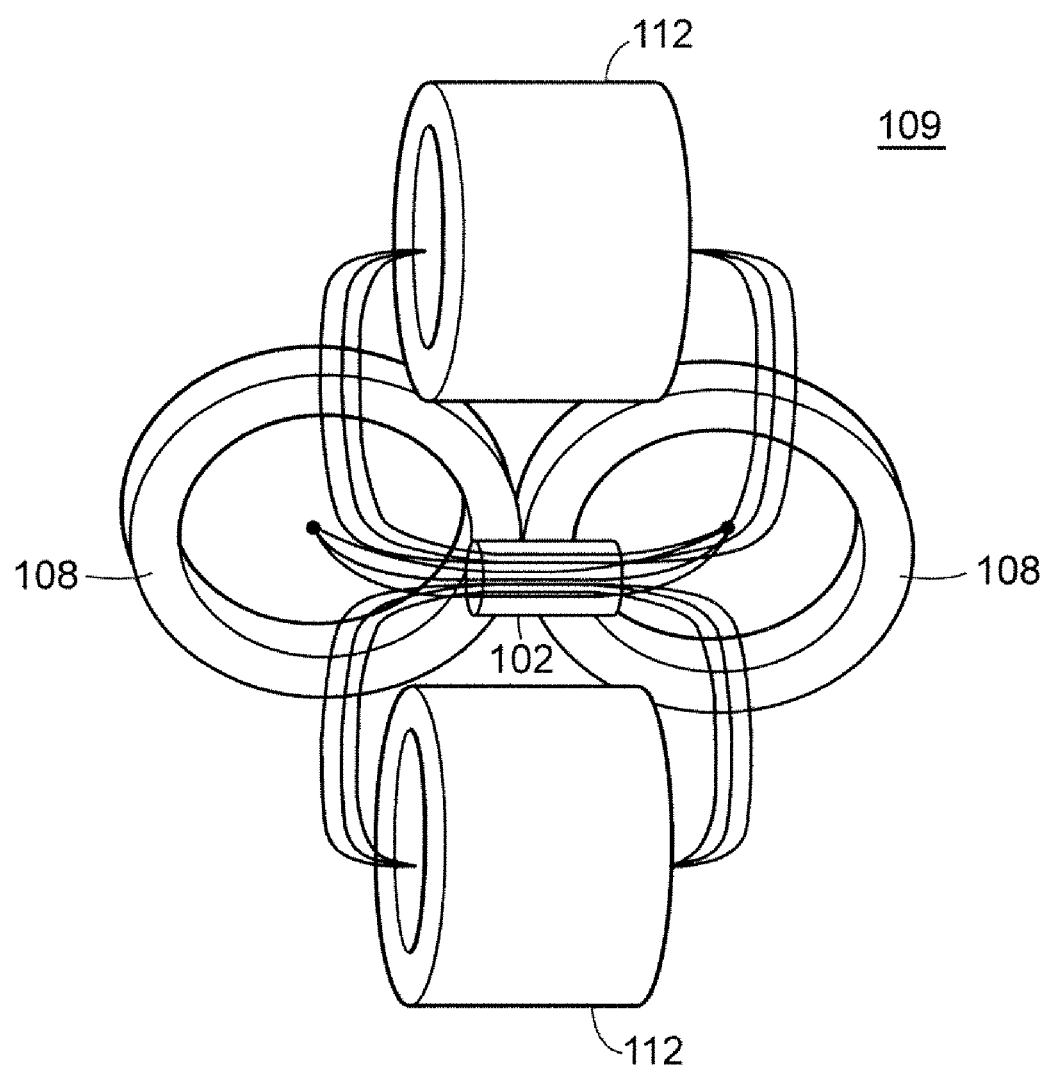
FIG. 16 illustrates an electromagnetic coil assembly for stimulating and detecting signals to and from the magnetoelastic sensor.

FIG. 1 illustrates an example system 100 for measuring a physical characteristic in a bile duct using a wirelessly transmitting magnetoelastic sensor. The system 100 generally includes a sensor 102 which in the illustrated example is a patterned mesh structure inside a self-expanding stent 104 that is to be placed in the bile duct. The sensor 102 is wirelessly stimulated by magnetic field lines 106 (shown by way of example) running along a length of the sensor 102 and generated by an external transmit coil assembly having two magnetic coils 108 as part of an external inductive coil assembly 109. A time-varying magnetic field from these transmit coils 108 stimulates all or a portion of the sensor 102, which then vibrates in response thereto. The vibration of the sensor 102 generates a magnetic flux that varies with a value of a physical characteristic within the stent 104, such as the sludge accumulation in the bile duct or the viscosity of fluid flow through the bile duct. A generated magnetic field 110 results from the sensor 102. Receive coils 112 are positioned in an orthogonal symmetry to the transmit coils 108 to detect the generated magnetic field 110. A network analyzer 114 controls the entire assembly 109 and receives the generated signal for determining the actual value of the physical characteristic being measured. FIG. 16 shows another view of an inductive coil assembly 109. The time-varying magnetic field may be a pulsed field, and impulse signal, or a continuous wave field.

In the illustrated example, the network analyzer 114 is connected to a computer 116 that receives data from the network analyzer, including the load values created by the generated magnetic field 110, and analyzes that data to determine a value of the physical characteristic being measured, e.g., viscosity or accumulated mass. The computer 116 then performs a data analysis to determine, e.g., whether the physical characteristic is in a warning region from which action should take place. The computer 116 may use threshold conditions that indicate when flow patency has dropped below a predetermined level. These threshold conditions may be determined in a standardized manner or based on baseline measurements particular to each patient, for example by comparing measured data against measured data taken at initialization, upon introduction of the stent and sensor device.

Figure 2:
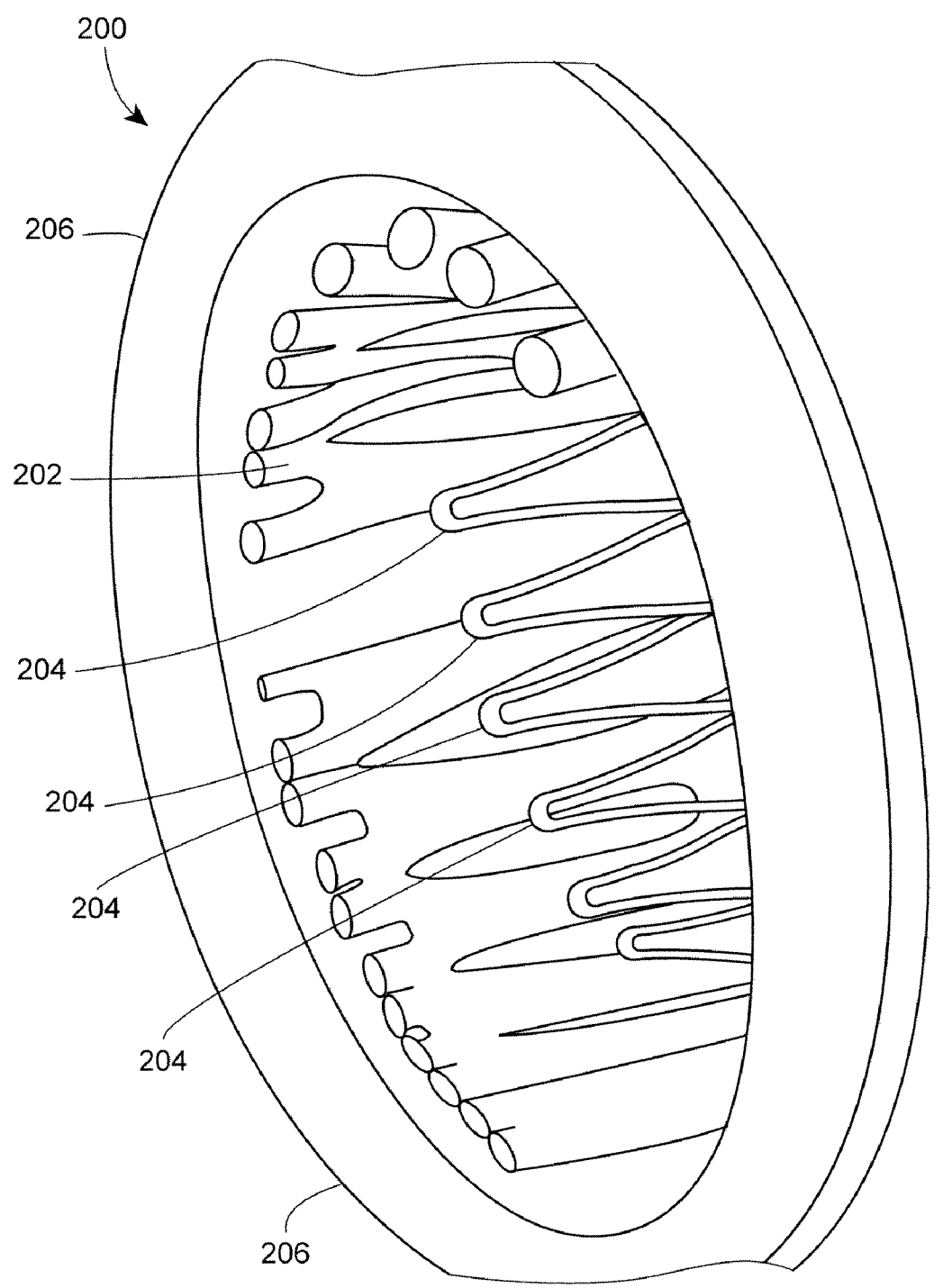
FIG. 2 illustrates a stent and magnetoelastic sensor having a patterned mesh structure.
Figure 3:
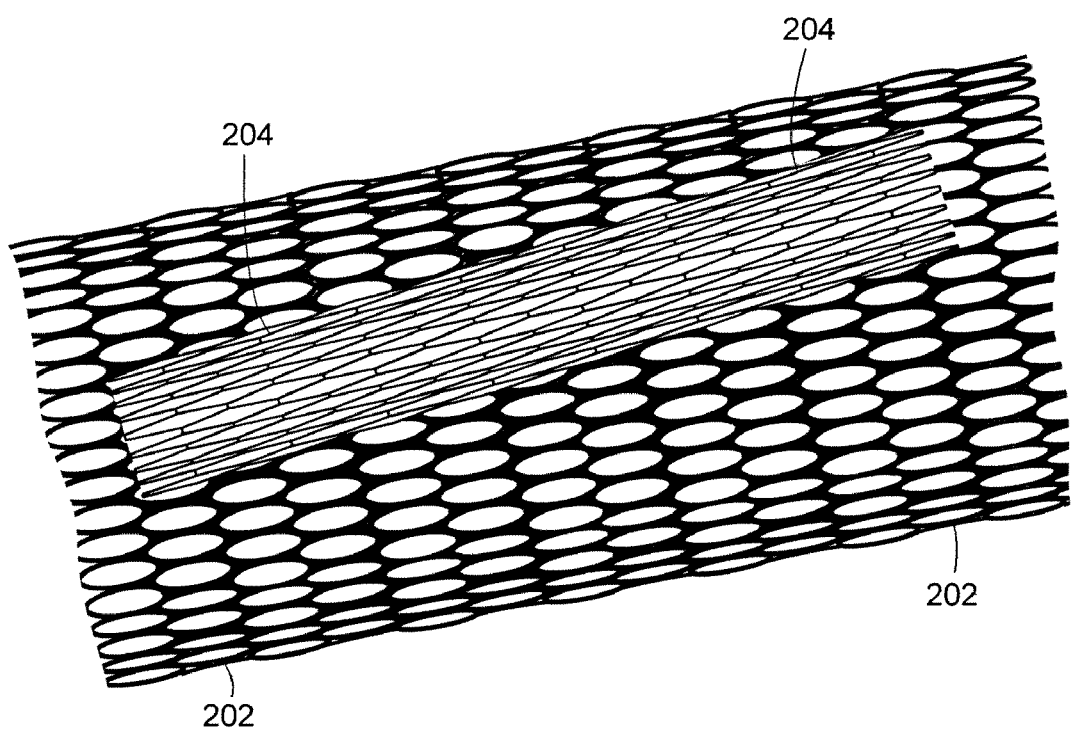
FIG. 3 illustrates another view of the stent and magnetoelastic sensor of FIG. 2 in an undeployed position.

FIG. 2 shows the end portion of an example implantable assembly 200 which includes a stent 202 and an integrated magnetoelastic sensor 204 inserted within the stent 202. The stent 202 would typically have a non-deployed state and a deployed state within the vessel. Stent 202, for example, has a tubular mesh structure when deployed, that structure having a mesh pattern as illustrated in one non-deployed position in FIG. 3. The sensor 204 is inserted within the stent 202 and has a patterned mesh structure surrounding a flow channel and formed of a magnetoelastic material that mechanically vibrates under application of a time-varying magnetic field. In this way, the variation in the frequency response of the generated flux may be correlated to the pathology characteristic to sense its value. Both the stent 202 and the sensor 204 are housed within an outer tubular housing 206 that is used to deploy these structures at a particular location in the bile duct or other vessel.

Figure 4:
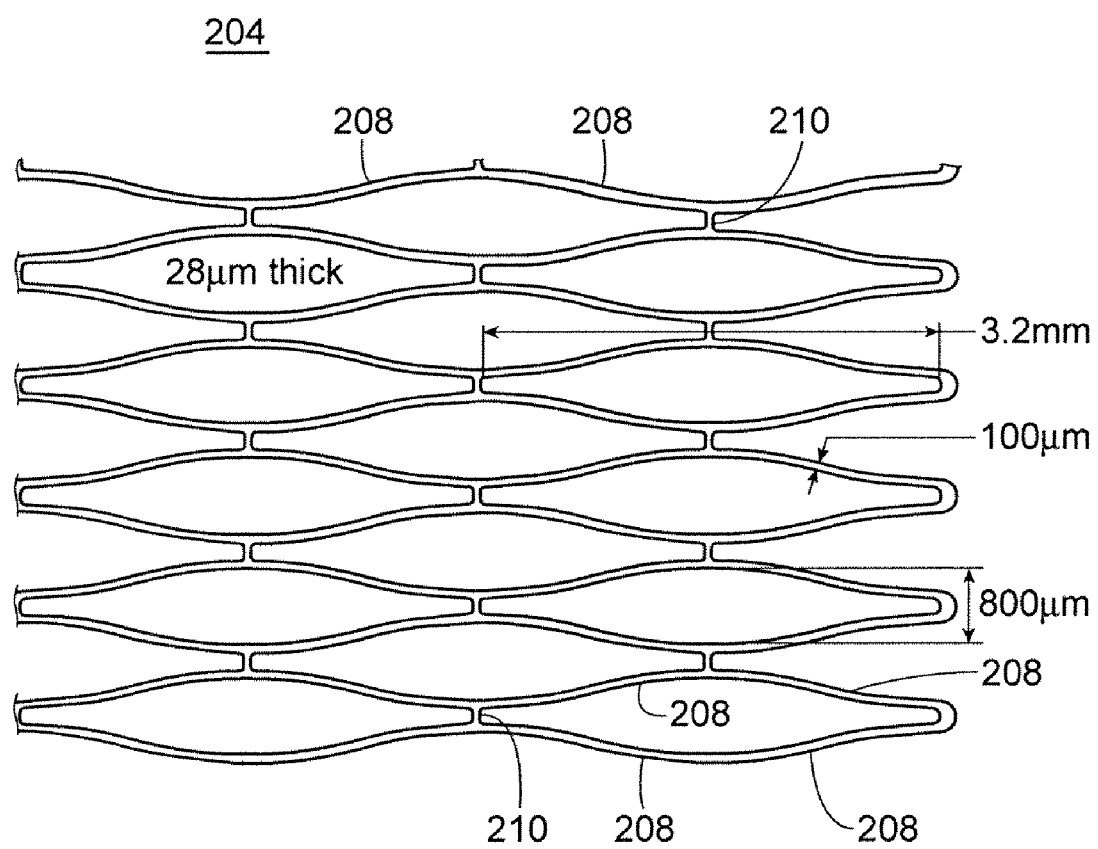
FIG. 4 illustrates an example close up view of the magnetoelastic sensor of FIGS. 2 and 3.
Figure 5:
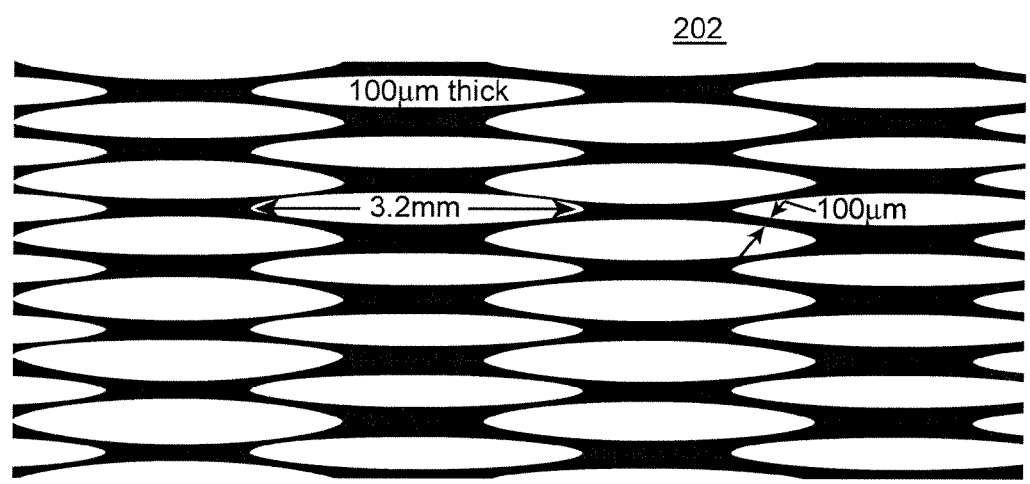
FIG. 5 illustrates an example close up view of the coated stent of FIGS. 2 and 3.

FIG. 4 shows the sensor 204 as having an elongated wishbone-array pattern, formed of elongated strut members 208 and connection point members 210 periodically disposed to connect these elongated strut members for forming diamond-shaped openings 212 in the pattern. FIG. 5 shows the stent 202 with a similar patterned mesh structure (i.e., wishbone-array pattern) and coated with a strontium-ferrite-PDMS coating. Using a patterned structure allows for good mechanical flexibility for both the stent and sensor while maintaining mechanical coupling and minimizing joint damping for efficient resonant operation of the sensor.

To ensure that plastic strain in the sensor was avoided during deformation that is required during catheter-based delivery, a finite element analysis (FEA) model was utilized. The fabricated dimensions are shown in FIGS. 4 and 5. The Young's Modulus used in the analysis was 130 GPa, the yield strain was 1.6%, and the Poisson's ratio was 0.2. With the fabricated dimensions, the FEA model suggests that the wishbone-array sensor can undergo a 50% reduction in circumference without plastic strain that may result in degradation of sensor performance. Because the magnetoelastic sensor will be called upon to operate in different vessels of differing dimensions, the magnetic responsiveness and sensitivity of that sensor should be maintained throughout these various operation conditions.

Because the wishbone-array pattern represents a significant departure from typical ribbon sensors, applicants developed an FEA tool that is appropriate for estimating mode shapes and expected signal amplitudes from sensors with complicated structures. The crux of this tool is in its use of linearized constitutive equations describing the coupling between flux, field strength, stress, and strain in a magnetostrictive material:

$$\vec{\sigma} = [C]\vec{\varepsilon} - \frac{[C][d]^T}{\mu_o\mu_r}\vec{B} \qquad (1)$$

$$\vec{H} = -\frac{[d][C]}{\mu_o\mu_r}\vec{\varepsilon} + \frac{1}{\mu_0\mu_r}\vec{B}. \qquad (2)$$

Equations (1) and (2) are versions of the so-called "piezomagnetic" equations—a name that highlights their similarity to piezoelectric equations—where $\sigma$ is the stress vector, C is the stiffness matrix, $\varepsilon$ is the strain, d is the magnetostrictivity matrix, B is the magnetic flux density vector, H is the field strength vector, $\mu_0$ is the permeability of free space, and PA is the relative permeability. Magnetostrictive materials are nonlinear, but linearization about an operating point in a resonant magnetoelastic analysis is prudent, with a rationale analogous to that used in small-signal models of transistor-based circuits. Equations (1) and (2) were implemented utilizing COMSOL Multiphysics and coupled time-harmonic (frequency response) induction current and stress-strain modes.

Figure 6:
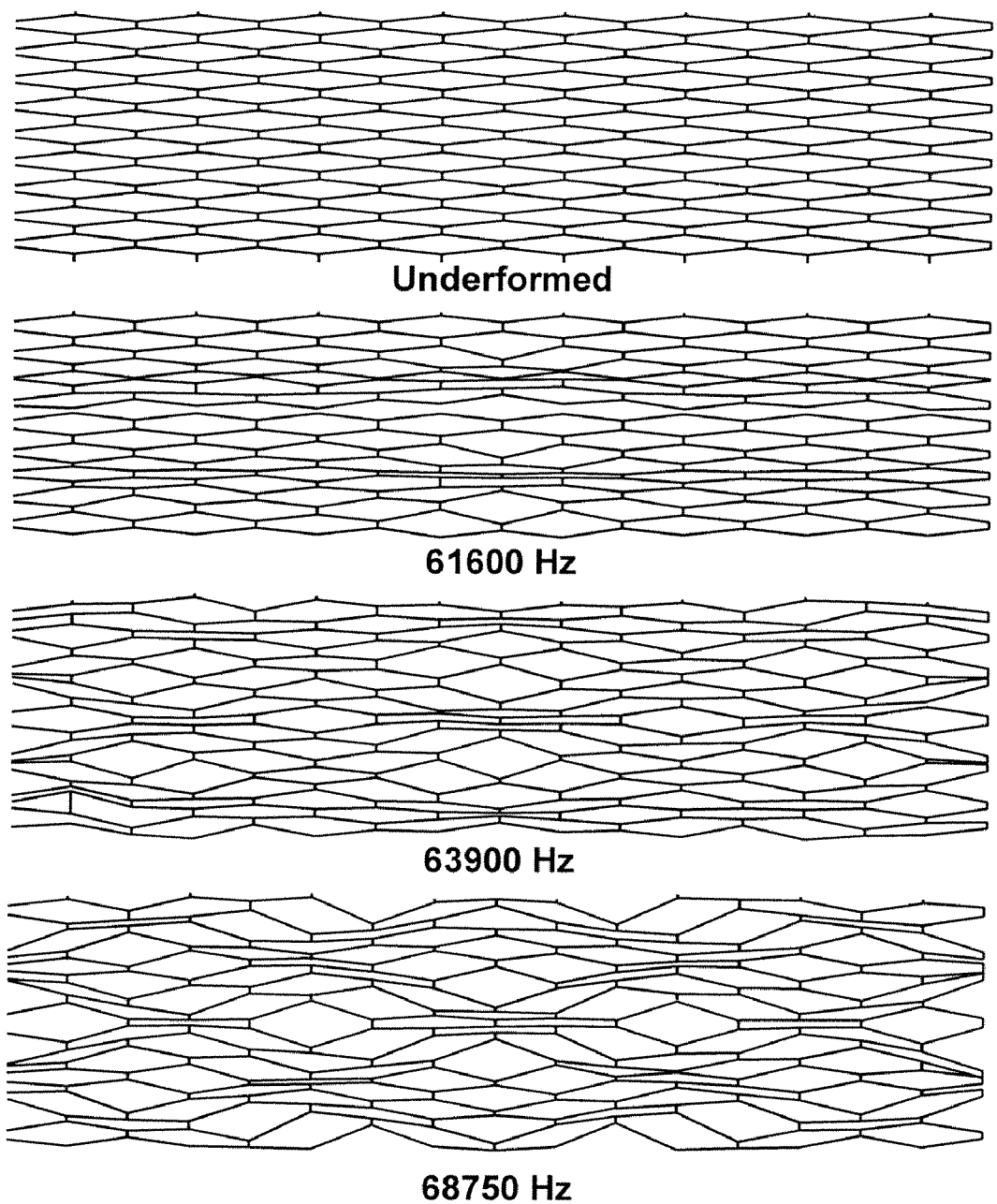
FIG. 6 illustrates calculated mode shapes and frequency predictions for a magnetoelastic sensor in an example.

FIG. 6 illustrates calculated mode shapes for planar wishbone-array sensors at four different stimulation conditions: 1) unstimulated where the sensor is "undeformed"; (2) the sensor stimulated by a magnetic field oscillating at 61.6 kHz; (3) the sensor stimulated by a magnetic field oscillating at 63.9 kHz; and (4) the sensor stimulated by a magnetic field oscillating at 68.75 kHz. The various mode shapes displayed are at frequencies corresponding to significant peaks in the measured frequency response for the planar sensors, with the mode shape at 61.6 kHz resulting in the largest response amplitude. Note that the mode shapes combine significant longitudinal and transverse motion on the sensor, whereas mode shapes of traditional ribbon sensors are limited to longitudinal motion. The model also predicts signal amplitude trends for various sensor geometries.

The sensors herein may be formed of any suitable magnetoelastic material. Example materials include Metglas™ alloys which have excellent magnetostrictive properties as well as excellent elastic properties. For instance, the 2826 MB alloy as used in some examples is reported to have a yield strain of 1.6% (J A. Lin, et al., "Embrittlement of Amorphous Fe40Ni38Mo4B18 Alloy by Electrolytic Hydrogen," Met. and Mat. Trans. A, Vol. 26, No. 1, 1995, pp. 197-201), which is even higher than most cold-reduced Elgiloy yield strains of ~1%. While useful as a magnetoelastic material, Metglas™ is not readily available in filament form. Furthermore, even with using a material like Metglas™ in filament form, a resonant sensor fashioned from braided filaments is likely to have low structural coupling and high damping at braid cross-over points. Therefore, a more preferred material approach is to form both the stent and sensor by batch-fabricating from foils of different base materials utilizing a photochemical machining (PCM) process, similar to that discussed in S. R. Green, et al., "Photochemically Patterned Biliary Stents with Integrated Permanent Magnets and Deformable Assembly Features for Wireless Magnetoelastic Tissue Growth Sensing," Transducers 2007. June 2007, pp. 213-217.

In an example implementation, patterned mesh sensors were batch fabricated from a 28 μm thick foil of 2826 MB Metglas™ utilizing the PCM process. Feature sizes of the elongated strut members were 100 μm, which is near the feature size limit for the technology. The overall size of the active portion of the sensor (not including the anchor areas) is approximately 7.5 mm×29 mm, with a mass of 9.1 mg.

PCM is a planar process, so the fabricated sensors were also planar. Because the stent application calls for a tubular shape, and the lateral dimension of the sensor is larger than the diameter of the stent, the sensor was curved into a tubular or semi-tubular shape to best match the stent geometry. While theoretically mechanical stress may be imparted to add curvature, initial testing led to achieving the tubular shape in this work by placing the sensor against the inner wall of a fixture tube and annealing for a period of time, e.g., 30 minutes. Various final radii may be achieved by either changing the fixture tube radius or by changing the anneal temperature. For instance, a 4.6 mm radius results from annealing at 375° C. for 30 minutes inside a 3.6 mm radius tube, while a 1.6 mm radius results from annealing inside a 1.25 mm radius tube, where generally speaking lower temperatures lead to lesser final curvature.

The stents were also batch fabricated using the PCM process, e.g., from a 100 μm thick foil of Elgiloy. As intended, the feature sizes and patterns were identical to those of the sensor. The overall stent size is 5 mm (dia.)×40 mm.

To affect sensor operation, in particular the concentration of mass at desired points on the patterned mesh structure of the sensor, various modifications may be made to a sensor design. FIG. 7A illustrates a sensor 300 having a first patterned mesh structure. FIG. 7B shows the sensor 300 undergoing stimulation and vibrating at first dominant mode shape having anti-nodal points 302 extending across the sensor 300 and corresponding to locations on the sensor body that experience the largest displacement at the resonant frequency. To improve operation of the sensor, its sensitivity to the pathological characteristic may be increased at these locations through various ways. FIG. 7C, for example, there have been mass-concentration increases 304 at the anti-nodal points 302 as a result of sensitivity control. In this instance, the surface area of connection points corresponding to the anti-nodal points 302 may be increased to allow for a great concentration of sludge in the bile duct to accumulate on the sensor, which would affect the responsiveness of the sensor.

FIG. 8 illustrates another example technique for controlling sensitivity of the sensor at particular locations. A sensor 400 is shown having elongated strut members 402 that terminate at connection points 404 some of which 404' are textured (see inset) to locally promote or inhibit protein and cell adhesion and increase vibration coupling to the viscous environment. In some examples only particular connection points 404 are controlled in this manner, such as the connection points corresponding to the anti-nodal points. In other examples fewer or more (including all) connection points may be so textured. Indeed, in some examples, the entire patterned mesh structure for the sensor 400 may be textured.

Figure 9A:
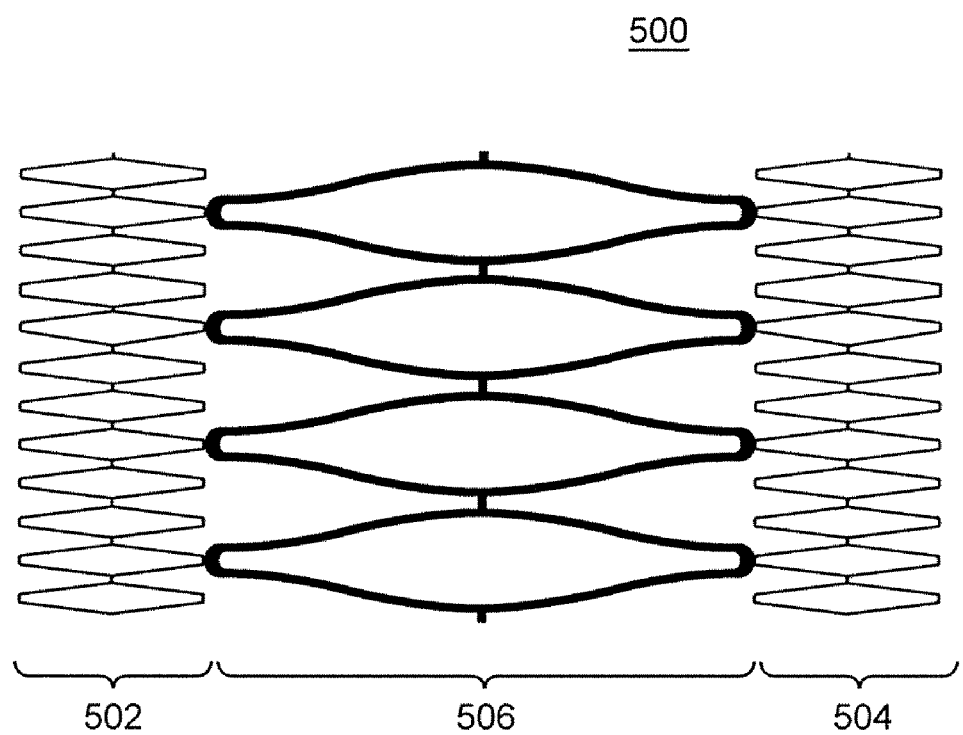
FIGS. 9A & 9B illustrate different magnetoelastic sensors having regions of different pattern density.
Figure 9B:
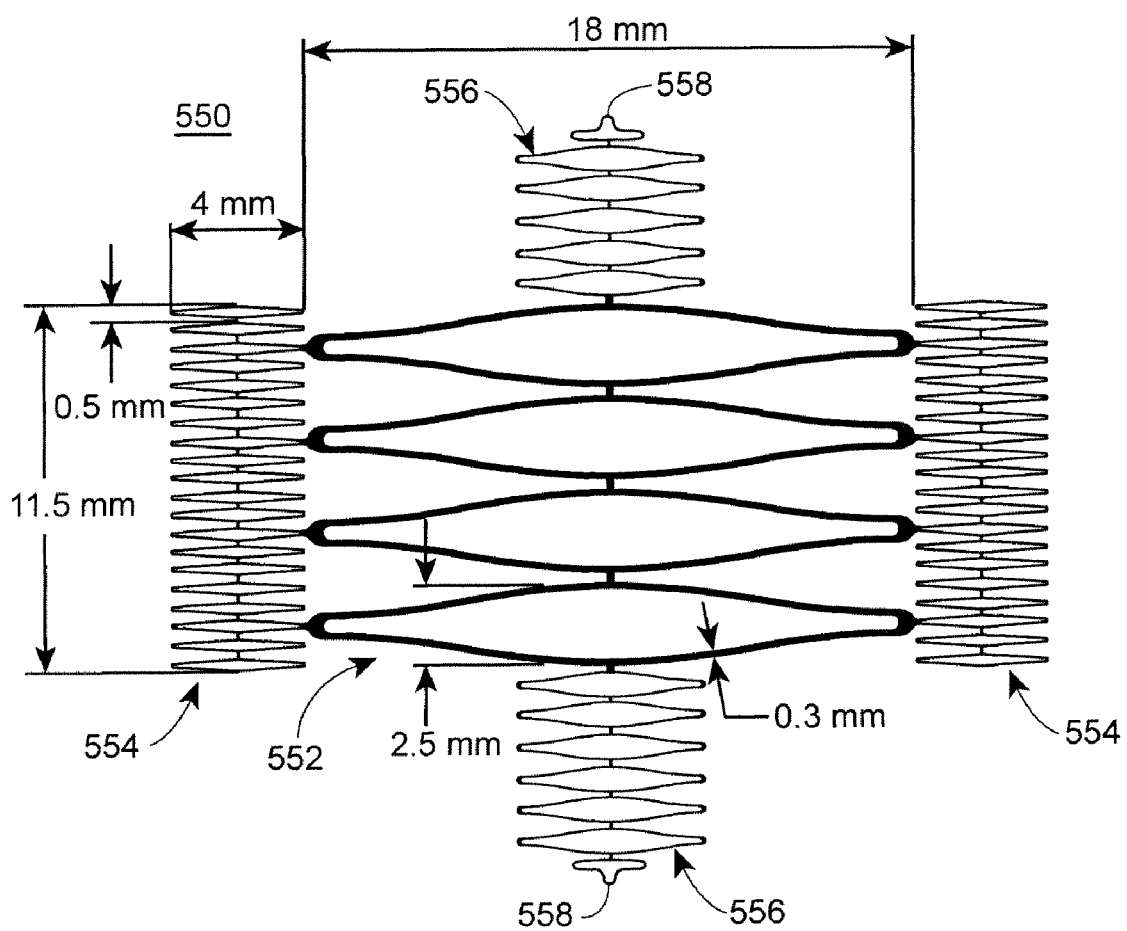

In some examples, the sensors herein have different regions having different vibrational responses which act to control operation of the sensor. FIG. 9A, for example, illustrates how pattern density may change across a sensor 500. First and second regions 502 and 504 may have a first pattern density, e.g., the number of lateral and/or longitudinal wishbone structures, while a central, intermediate region 506 between the two may have a different, lower density. The denser regions 502 and 504 will provide more surface area for cell adhesion and mass accumulation. Therefore these regions may be placed at desired locations, such as the anti-nodal points discussed above. FIG. 9B illustrates a sensor 550 similar to that of sensor 500 but with low-density pattern region 552 surrounded by first side regions 554 and second side regions 556, each having a higher density pattern in comparison to the region 552. The regions 556 have a lower pattern density than the side regions 554, thereby illustrating the structure as having varying density across the regions. Each region's pattern is a wishbone pattern in the illustrated example, although this need not be the case. The side regions 556 include a tether 558 for attachment to a stent.

Figure 10:
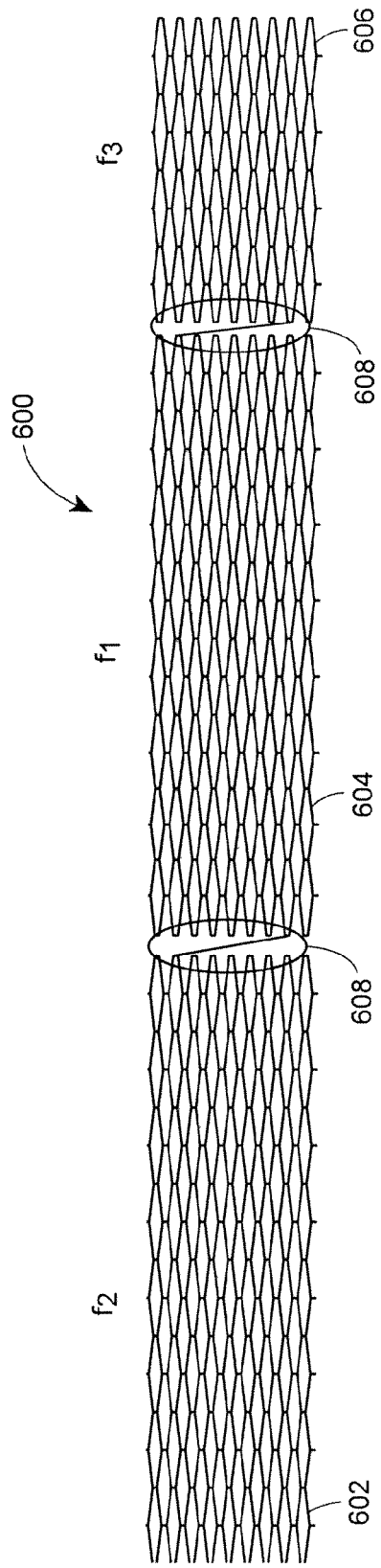
FIG. 10 illustrates a magnetoelastic sensor having regions of different resonant frequency.

FIG. 10 shows yet another example portion of a sensor 600. In this example, the sensor 600 includes three different regions, 602, 604, and 606 each having a different resonant frequency, as shown, and each connected to one other region by an intermediate connection in the form of a flexible coupling 608. The flexible coupling is designed to allow each region 602, 604, and 606 to operate independently. Thus, each region may vibrate in response to receiving an oscillating magnetic field signal at their particular resonant frequency. By partially decoupling regions in this manner, the sensor 600 may be designed to have different responsivities at different locations along the sensor 600, allowing for even more accurate locating of a mass accumulation or other pathological characteristic.

While using multiple patterned regions allows for precision control over the excitation modes and responsive of the sensor, each individual region or for that matter a single patterned structure like that shown in FIG. 7A can be formed of a sufficient cell structure and dimensions to have varying spatial sensitivities. Thus different magnetic fields—in frequency or orientation—may excite different portions of a single, uniform patterned structure.

Figure 11:
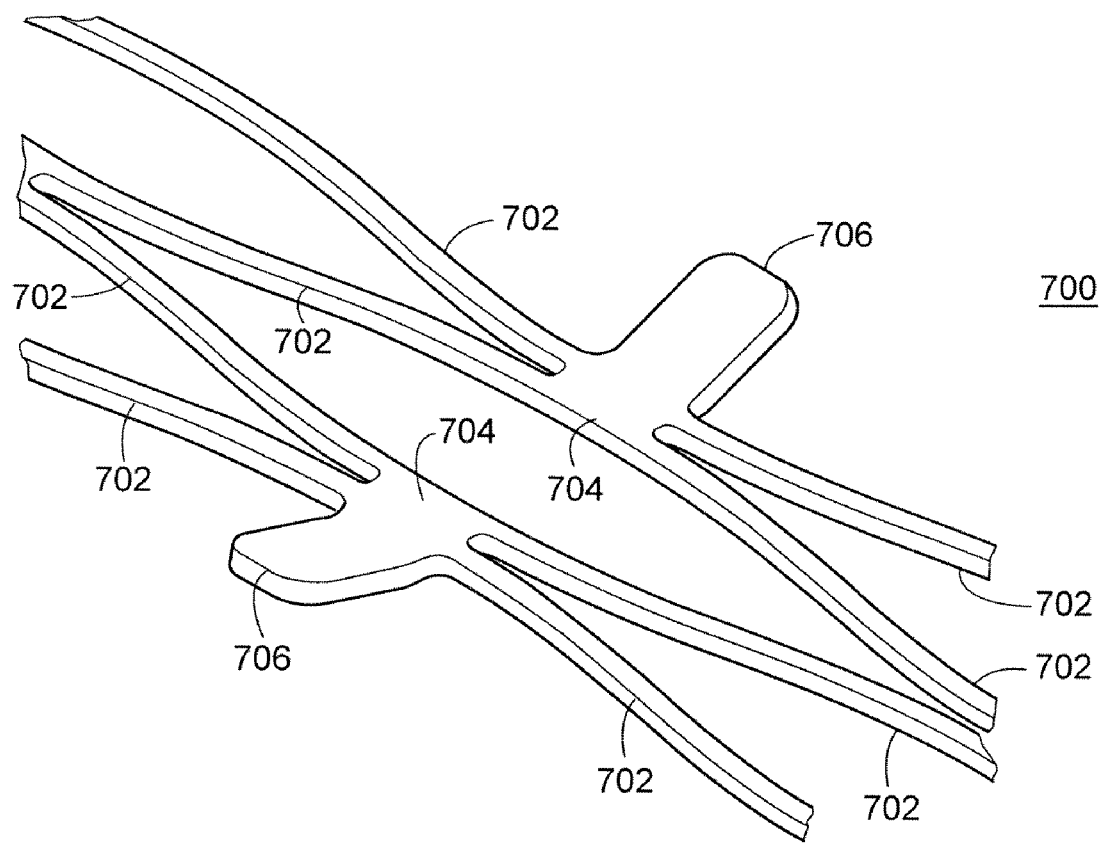
FIG. 11 illustrates a magnetoelastic sensor having winged regions of increased sensitivity.

FIG. 11 shows yet another technique for increasing the sensitivity of the sensor to a pathology characteristic. In this instance, sensor 700 includes elongated strut members 702 which form a wishbone pattern, although only a portion of the patterned sensor structure is shown. The sensor 700 is different in that at connection points 704, winged flanges 706 extend out from the sensor, substantially orthogonally to the longitudinal axis of the sensor 700. These flanges 706 help enhance coupling of the sensor to the environment, for example, by causing some parts of the sensor to protrude out-of-plane to move more of the surrounding fluid as the sensor vibrates.

Figure 12:
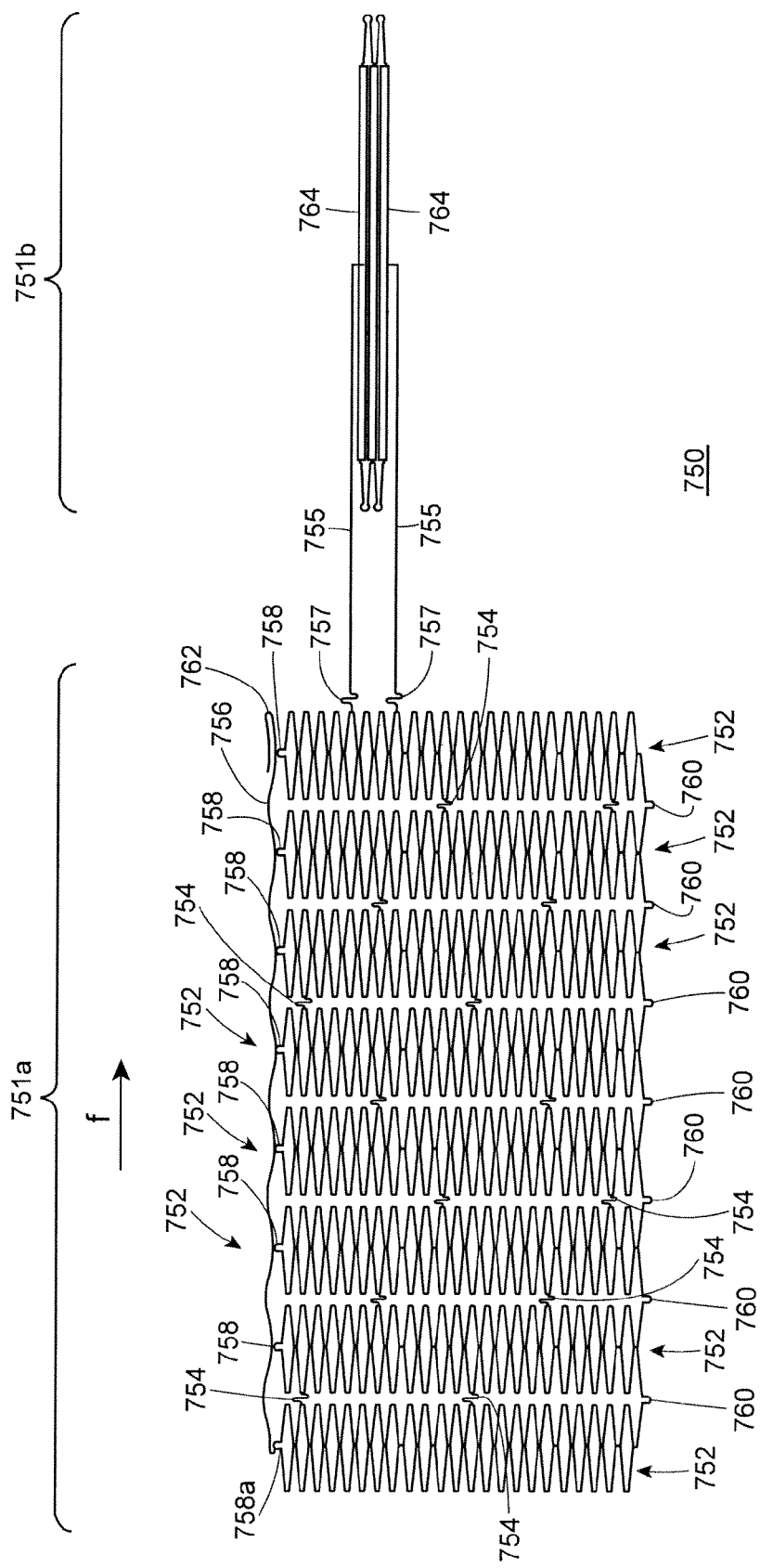
FIG. 12 illustrates a stent device with monolithically integrated magnetoelastic sensor in a planar, non-deployed position.
Figure 14:
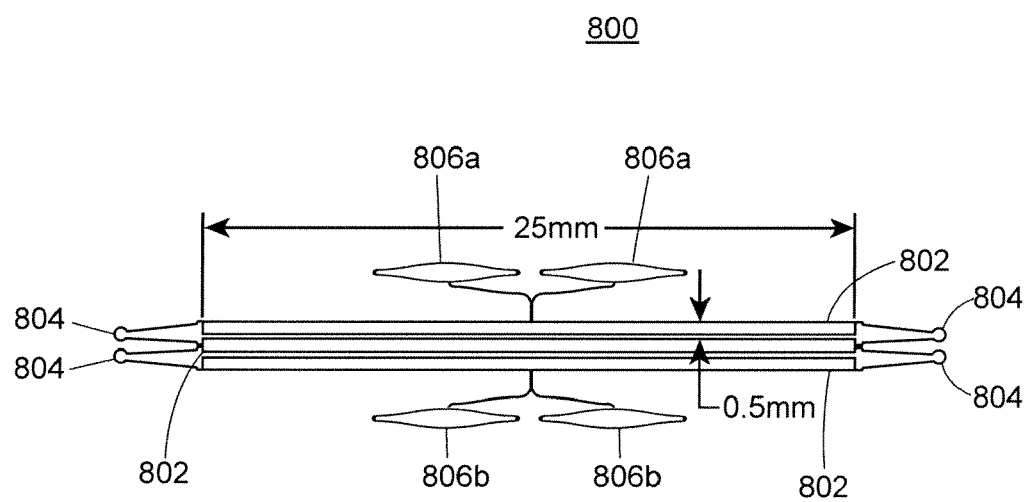
FIG. 14 illustrates a magnetoelastic sensor in a hybrid ribbon configuration.

FIG. 12 illustrates an integrated stent and sensor device 750 in a planar, pre-deployed position. The device 750 is considered monolithic in that a stent portion 751a and sensor portion 751*b* are initially fabricated from one contiguous substrate. In such a device, the stent 751*a* and sensor 751*b* may be of the same material (or material composite), or well-known techniques can be used to selectively deposit and remove layers of materials to and from each portion to impart function-specific properties. For example, the sensor portion 751*a* and stent portion 751*b* can be formed from a base layer of chrome-nickel foil, and magnetoelastic material can then be selectively deposited on the sensor portion to impart the necessary magneto-mechanical coupling in the sensor portion. FIG. 14 illustrates an example of a hybrid magnetoelastic sensor that can be used for the sensor portion 751*b*. It will be appreciated that any patterned structured sensor, including the others illustrated herein, may be similarly monolithically formed with the stent.

In the illustrated example, the stent portion 751*a* of the device 750 is formed of a patterned structure having a plurality of interconnected regions 752, each formed with a wishbone array pattern containing wishbone (or "diamond") shaped cells extending laterally across the sensor 750. Each region 752 may be identical to the others, for example, with the same pattern density, as shown. Or the regions 752 may be different in cell pattern or pattern density. Each region 752 is coupled to another region using one or more switchback pattern connectors 754 (only some are labeled), which are positioned to improve bending flexibility of the stent portion of the device. In the illustrated example, each wishbone cell (each region comprising 23 cells in the illustrated example) may be approximately 1 mm in length in the lateral direction and 5.5 mm in length in the longitudinal direction, which direction would also be the direction of fluid flow, f, through the device during deployment.

The sensor portion 751*b* of the device 750 can be folded over such that the sensor portion 751*b* is positioned above the stent portion 751*b*. The connecting beams 755 and beam joints 757 can be designed such that, after folding, the sensor portion 751*b* remains in place via plastic deformation of the beams 755 and beam joints 757. Alternatively, the sensor portion 751*b* may be physically joined with the stent portion 751*a* after folding with localized bonds, welds, or mechanical assembly joints.

Figure 13:
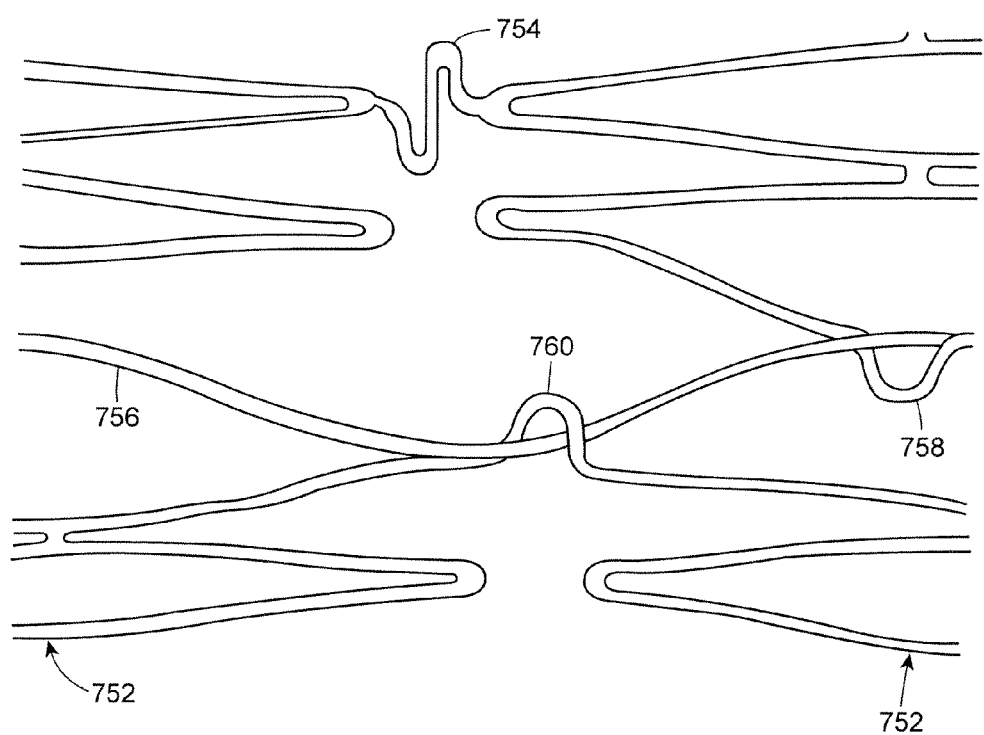
FIG. 13 illustrates a portion of the device of FIG. 12 in a deployed position.

After the sensor portion 751*b* is disposed above the stent portion 751*a*, the device 750 may be repositioned from the planar position shown to a deployed position—for example, a tubular shape for insertion into a bodily vessel. To facilitate deployment of the device 750, a loop and wire configuration is used. Capping a first half of the regions 752 is an integrated wire 756. Specifically, the wire will be threaded through loops 758 positioned on the same half (top half) of each region 752. Similarly, in the deployed position, the integrated wire 756 will be threaded through loops 760 at the opposite half (the bottom half) of the regions 752. To facilitate this threading, the wire 756 is coupled to a first loop 758*a* at a proximal end and has a locking feature 762 at a distal end thereof. FIG. 13 illustrates a portion of the monolithically integrated device 750 in a deployed position, illustrating the threading of the integrated wire and loop configuration.

FIG. 14 illustrates another magnetoelastic sensor in the form of a hybrid ribbon sensor 800. The hybrid ribbon sensor 800 is an elongated sensor formed of a plurality (three) of ribbons 802 formed of a magnetoelastic material and spaced apart from one another transversely, but mechanically coupled at ends by couplers 804. These couplers 804 provide mechanical connection between the ribbons 802 while maintaining sufficient flexibility in the pattern to undergo the deformations required for deployment of the stent and sensor. The couplers 804 also allow for mechanical vibrational force transfer from one ribbon to another, where coupling increases the amplitude of the vibrations and thus increases the wireless range of the sensor 800. To attach the ribbon sensor 800 to a stent, anchors 806 are used, two opposing anchors 806*a* are positioned on a first side of the ribbons 802 and two other opposing anchors 806*b* are positioned on a second side of the ribbons 802. While three ribbons are shown, any number of ribbons can be used with corresponding numbers of couplers. Increasing the number of ribbons may provide a greater surface area for sensing the physical pathological characteristic, and may additionally increase the signal amplitude from the sensor.

As shown in the various figures above the patterned mesh structure sensors herein may have a plurality of different regions extending along an elongated length and which vary in response to physical pathology characteristics in a vessel. For example, these regions may differ in density, length, and pattern shape. For the latter, for example, some regions may have a wishbone array pattern, while other regions may have other patterned mesh structures. The mass loading effects and viscosity response of each region may thus be made to vary.

It is also noted that the changes made to the sensitivities of portions of the magnetoelastic sensors may be made to promote mass accumulation, for example, by increasing sensitivity at anti-nodal points, or to inhibit accumulation, for example, by increasing sensitivity everywhere but at the regions of highest sensitivity. For example, if a physical pathological characteristic is accumulated mass or viscosity, then regions of increased sensitivity on the patterned mesh structure can include: an increased surface area of the patterned mesh structure at locations on the patterned mesh structure to promote mass accumulation; increased surface area of the patterned mesh structure at locations on the patterned mesh structure to inhibit mass accumulation; selective application of a material coating to the patterned mesh structure at locations to promote mass accumulation; selective application of a material coating to the patterned mesh structure at locations to inhibit mass accumulation; selective application of surface texture to the patterned mesh structure at locations to promote mass accumulation; and selective application of surface texture to the patterned mesh structure at locations to inhibit mass accumulation. These modifications are provided by way of example, as other techniques may be used.

Various sensing modalities result from this adaptability of the present techniques. For example, by applying an oscillating stimulation magnetic field to a first resonant frequency of the first region, the sensor can parametrically convert vibrational energy generated in the first region to vibration energy generated in the second region, within which the sensor generates a transmitting magnetic field at a second resonant frequency that is different than the first resonant frequency.

In some examples, applying the stimulation magnetic field will generate a first signal in the first region. The sensor will communicate the first signal in the first region to the second region within which a second signal is generated, from which the system may measure a time delay between received first and second signals to measure a time-of-flight value correlating to the value of a physical pathology characteristic in a vessel. In other examples, a frequency shift between the first and second signals is measured and could be correlated to the value of a physical pathology characteristic in a vessel.

The various measurement techniques described herein may involve sensing the physical pathology characteristic in the vessel and then correlating the sensed value of that characteristic (as measured by the sensor) to a value of the pathology characteristic, for example, by accessing a look up table or calculating the value from a predetermined correlation formula. Such analysis may be achieved in the network analyzer or other computer equipment.

To achieve optimal magnetomechanical coupling, the magnetoelastic sensor should be biased with a DC magnetic field. This field offsets the as-fabricated anisotropy of the magnetic domains in the sensor material; and the optimal field is dependent not only on the material of the sensor, but also on the feature sizes or aspect ratio of the final sensor. The process of selecting a bias field magnitude can be considered analogous to selecting an operating point for a transistor in an electrical circuit.

The applicants have developed techniques for integrated discrete magnets that showed that sensor performance is improved when the bias field is as uniform as possible. This uniformity is difficult to achieve with integrated discrete magnets, however, because the field strength will necessarily decay as the distance from the magnets increases. Therefore, continuously-distributed magnetic fields may be used to provide a more uniform field strength, to improve sensor performance and eliminate high magnetic field gradients that lead to undesirable magnetic forces.

One technique for achieving such uniformity is a conformal magnetic layer. The conformal magnetic layer is one that coincides exactly, within fabrication tolerances, with the shape of the stent over at least some portion of the length of the stent. This conformal layer may coincide at a single location, continuously throughout, or periodically at different locations of the stent. The layer does not otherwise disrupt the shape of the stent, following its natural curvature. Additionally, the stent does not have to be reshaped to accommodate the magnet. The conformal layer may provide uniform magnetic field distribution about an inner radius of a stent and along the longitudinal axis thereof. A distributed magnet was designed as a layer of strontium ferrite (SrFe) particles (~1 μm average diameter, Hoosier Magnetics) suspended in polydimethylsiloxane (PDMS, Sylgard 184, Dow Corning) and integrated or embedded on a surface of a stent having tubular structure. The polymer-suspended particles may be applied in a thin, flexible layer conforming exactly to the stent structure as shown in FIG. 5.

Other polymers have been used as a base for SrFe particles in micro fabricated magnets described elsewhere. See, e.g., L. Lagorce, et al, "Magnetic and Mechanical Properties of Micromachined Strontium Ferrite/Polyimide Composites," JMEMS, Vol. 6, No. 4, 1997, pp. 307-312. SrFe particles have the advantages of being chemically inert (owing to their ceramic nature), and of being widely and inexpensively available in very small particle sizes. The chemical inertness is especially valuable for this implantable application. PDMS is chosen in this work due to its generally accepted biocompatibility and due to processing ease. In fact, the entire polymer-suspended magnet fabrication process (as described later) is preferable in terms of ease compared with alternative options such as sputtering or electrodeposition of a thin-film magnetic layer.

To form the conformal magnetic layer, in an example, the PDMS was first mixed in a 10:1 base-to-curing-agent ratio. Subsequently, the SrFe particles were introduced in 1:1, 3:1, or 1:3 SrFe-to-PDMS by weight ratios and mixed in by hand until the mixture was consistent (usually about 1 minute of mixing time). The mixture was then poured or spread into a mold containing the stent. The stent was then pealed out of the mold, with a conformal layer of the magnetic suspension adhered due to surface tension. The layer was then cured for 30 minutes at 60° C. Thicker layers can be built up by repeating the process. Finally, the layer was magnetized uniformly along the longitudinal axis of the stent using a benchtop pulse magnetizer. In general, the 1:1 SrFe:PDMS ratio offered the best combination of workability and remnant strength of the ratios tested.

Figures 15A, 15B:
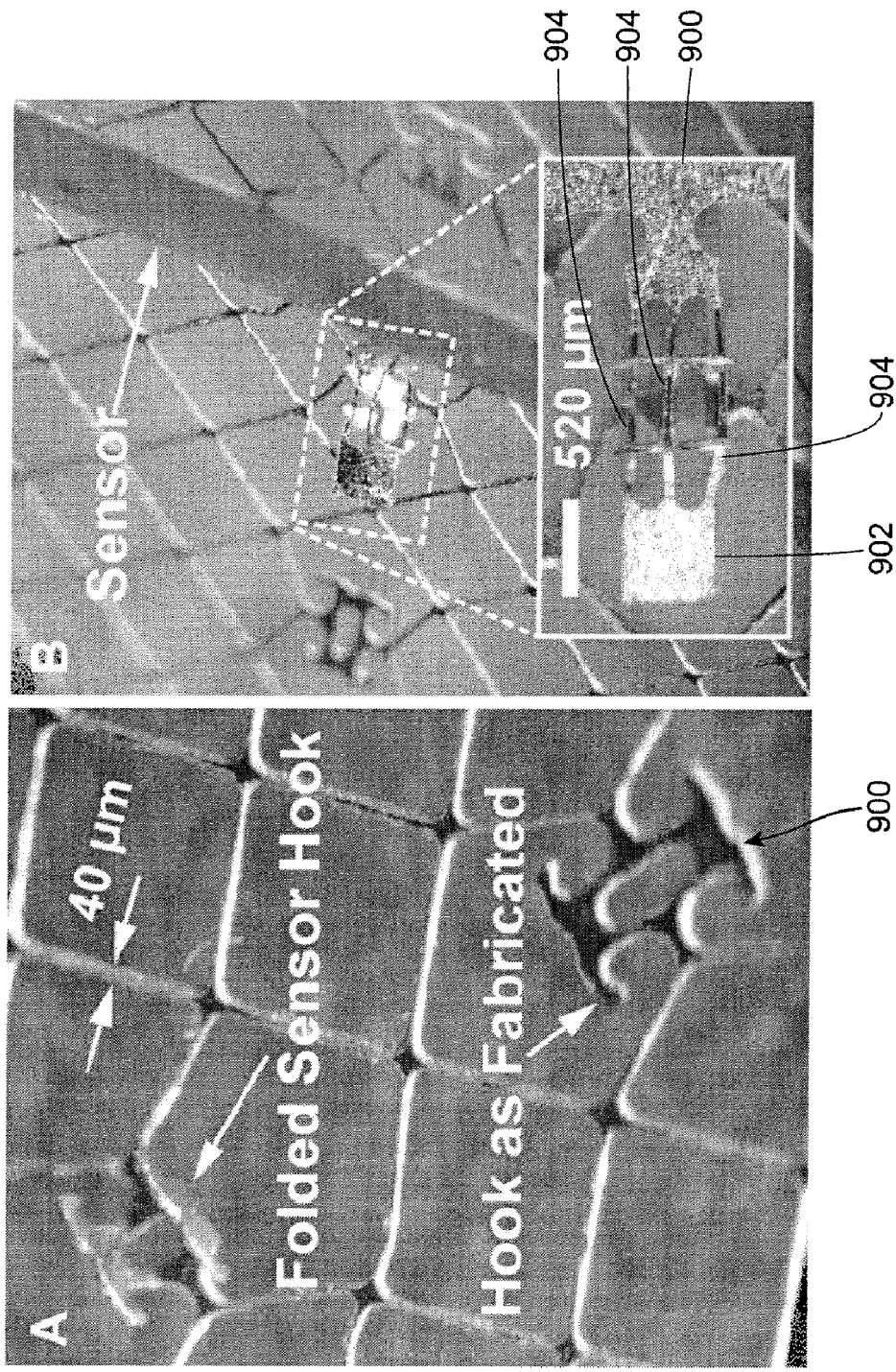
FIGS. 15A and 15B illustrate hook mechanisms for attaching the magnetoelastic sensor to a deployable stent.

While the sensor may be placed within the stent without any intended direct coupling between the two, in other examples a coupling may be achieved by providing spacers on an outer surface. Spacers (or standoffs) may be used to space an outer surface of the sensor from an inner surface of the stent, for example, by 100 microns or less to allow for sufficient mass concentration collection but also the desired longitudinal and transverse movement of the sensor as endemic to the various resonant modes. For example, FIGS. 15A and 15B show sensor attachment hooks 900 (folded and as fabricated) that are formed on the stent to provide a suspended base 902 that may be attached to the sensor inside the stent, the base extending from suspension arms 904 connected to the mesh structure forming the stent. These attachment hooks 900 may be positioned periodically in a patterned manner around the inner surface of the stent for attachment to the sensor.

For example, lateral portions of a wishbone-array sensor may be connected to the active area with single struts. These areas act as anchors, and the single struts isolate the vibrating active area from the anchors. The anchors of the sensor are bonded to the stent with a thin layer of PDMS applied between the anchor and the base 902. Subsequently, the stent is rolled into a tubular shape and the resulting seam where the edges of the stent adjoin is also bonded with a thin layer of PDMS. The process was used to develop the assemblies shown in FIGS. 2 and 3.

The fabrication process may thus include the following steps: A) PCM patterning of Elgiloy (stent) and Metglas™ (sensor); B) Stent coated in SrFe-PDMS layer and magnetized, and the sensor is annealed in a tube; C) sensor anchors bonded to stent with PDMS; and D) stent seam bonded with PDMS.

In other examples a mechanically decoupling layer may be disposed between the sensor and the stent to allow mechanical vibration of the sensor in longitudinal and transverse directions but maintaining general positional coherence between the two structures.

Figure 17:
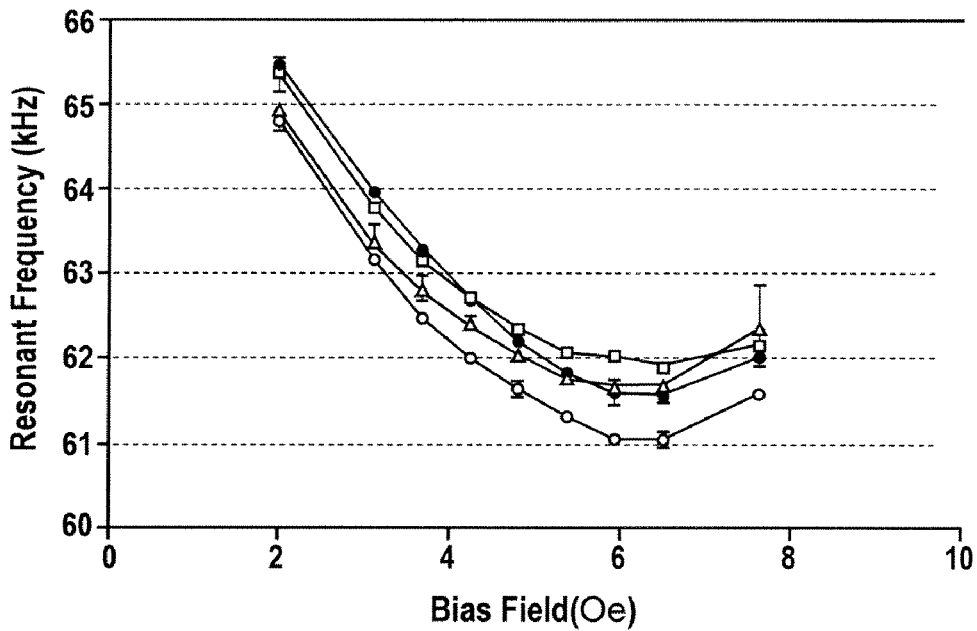
FIG. 17 is a plot of biasing magnetic field versus resonant frequency for a magnetoelastic sensor.

Prior to integration, as-cast planar sensors were evaluated using a uniform but variable bias field applied by Helmholtz coils located coaxially with the long axis of the sensor. For all tests, a swept-frequency network analyzer signal was amplified and sent through a transmit coil, while the same analyzer measured the EMF generated on a receive coil. The sensors were located concentrically with these coils. Results from the initial evaluation for the largest modal response of four sensors are shown in FIG. 17. The four plotted lines represent the mean of three trials each, where the error bars represent the minimum and maximum recorded values. The four plotted curves represent four sensors from the same manufacturing run undergoing the same characterization. The optimal bias field, where the amplitude of the response is largest (10 mV), is around 5 Oe. A clear dependence of resonant frequency on bias field can be seen—a manifestation of the ΔE effect. The frequency and amplitude show repeatable performance across the tested sensors, as do frequencies and amplitudes from other modes, indicating a repeatable PCM fabrication process.

Figure 18:
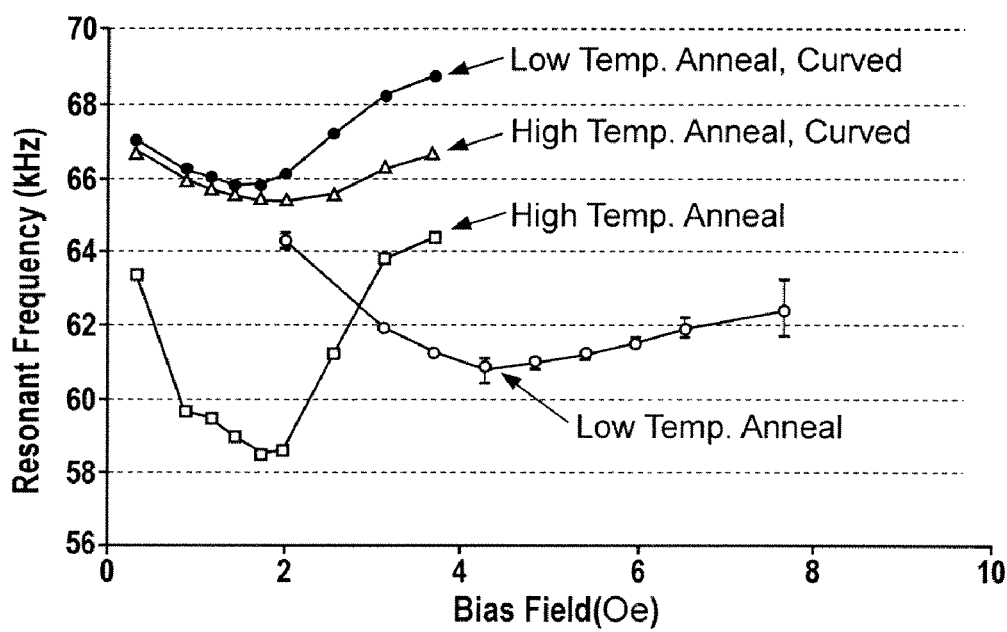
FIG. 18 is a plot of biasing magnetic field versus resonant frequency for different annealing conditions on a magnetoelastic sensor.

The sensors were then thermally treated either above (375° C.) or below (325° C.) the material Curie temperature (353° C.) and either remain planar or were given curvature. Post-treatment evaluation showed lower optimal biasing field, and an improved signal level compared to sensor performance prior to treatment. This important result shows that thermal treatment facilitates thinner SrFe-PDMS layers, which simplifies fabrication and minimizes concerns about large chronically implanted magnetic fields. FIG. 18 shows the relevant data characterizing the wishbone-array sensor after thermal treatment.

As-cast and thermally treated sensors were compressed through 1.5 mm diameter tubes—a circumferential deformation of at least 37%—without signal degradation. The repeatable performance of this test across both as-cast and thermally treated sensors implies that the thermal treatment process does not lead to impaired mechanical properties. The slight discrepancy with the FEA model predictions may be due to an imperfect correlation between the onset of plastic strain and the onset of strains that change the magnetomechanical properties of the material.

Figure 19:
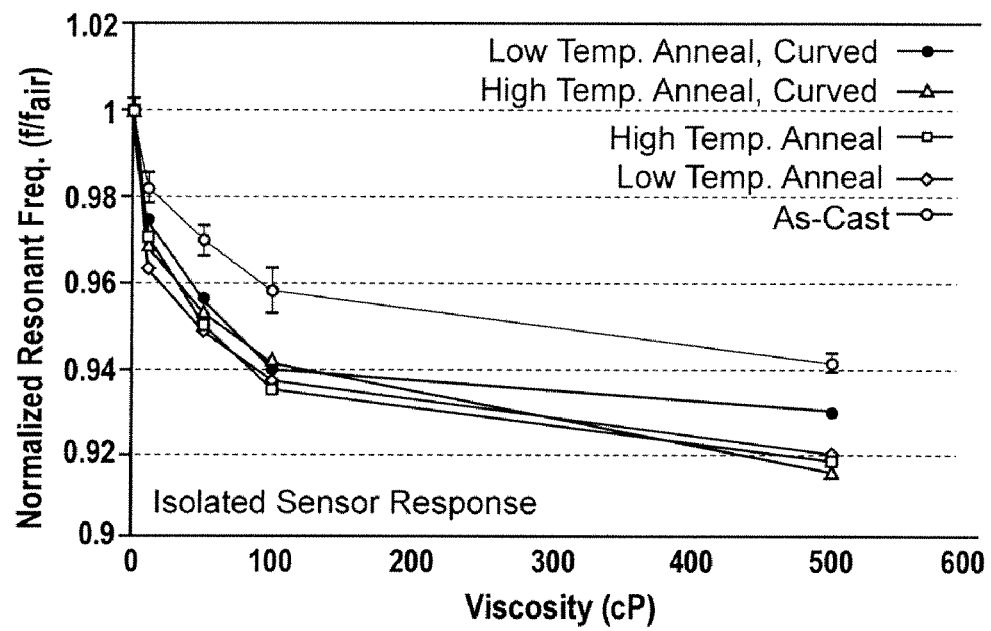
FIG. 19 is a plot of viscosity versus a normalized resonant frequency for a magnetoelastic sensor.

Bile viscosity changes are precursors to sludge accumulation, so sensor response to viscosity was evaluated (FIG. 19). The tested viscosity range is much greater than the physiological range of bile (1-12 cP), but the results show that sensitivity and signal amplitude is maintained over a very large range that might be suitable for other applications. Note that a 2.5 mm×37.5 mm ribbon sensor resonant frequency will drop by only 6% over this viscosity range.

Figure 20:
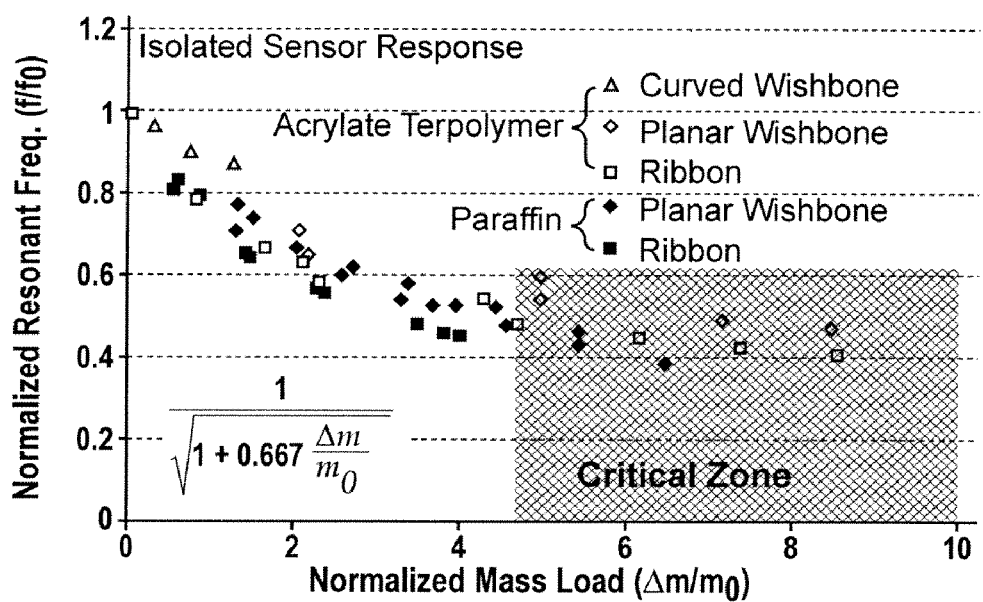
FIG. 20 is a plot of normalized mass load versus normalized resonant frequency for a magnetoelastic sensor.

Accumulation of sludge results in a mass-loading effect on the sensor. This process was simulated by the application of two different materials—paraffin and a spray-on acrylate terpolymer—to as-cast and thermally treated wishbone-array sensors, as well as to 2.5 mm×37.5 mm ribbon sensors. As shown in FIG. 20, each of the sensor types reacts similarly in terms of resonant frequency to both sludge simulants. Further, the full scale range of each sensor type extends into the "critical zone", where accumulation begins to significantly narrow the cross-sectional flow area.

Figure 21:
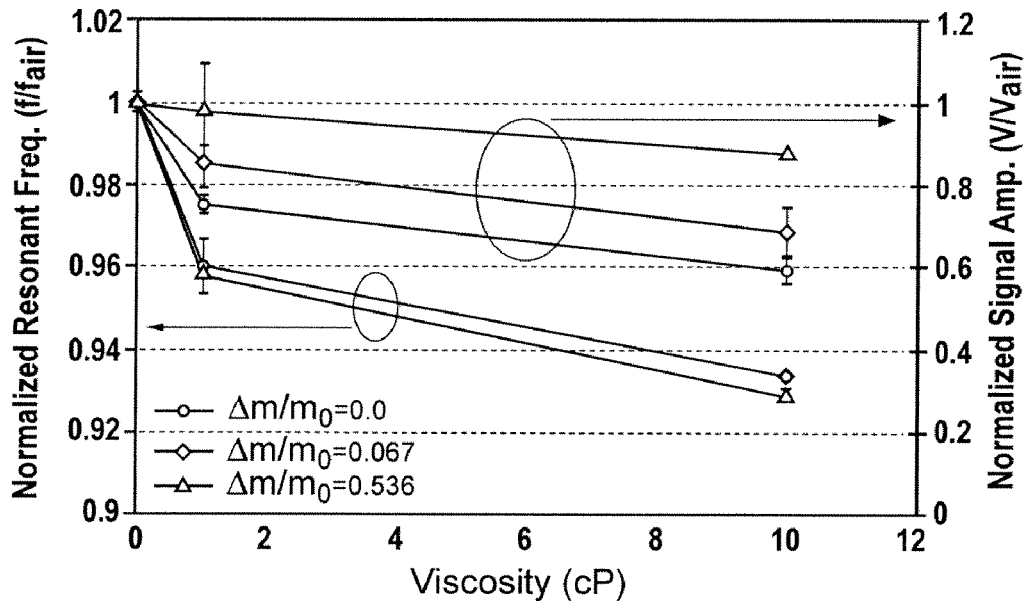
FIG. 21 is a plot of a response of sensing system to viscosity changes as mass accumulates on a magnetoelastic sensor.
Figure 22:
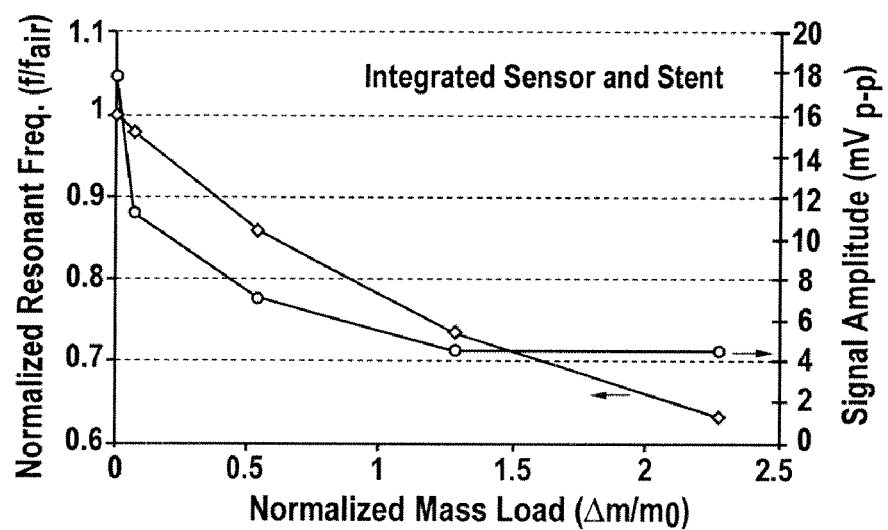
FIG. 22 is a plot of a response of a system to mass buildup.

In another experimentation, the integrated system included a curved wishbone-array sensor and a SrFe-PDMS coated stent. The system was evaluated in a manner similar to the isolated sensors above, but without the bias field supplied by the Helmholtz coils. In this way, all biasing of the sensor was provided by the conformal SrFe-PDMS magnetic layer. For the integrated system, sensitivity to viscosity over a physiologically appropriate range was measured even as mass was added. This experimental process showed that the normalized frequency response of the sensor to viscosity changes was not significantly affected by mass buildup (FIG. 21). Application of the acrylate terpolymer sludge simulant as a mass load showed that the frequency and signal amplitude of the integrated sensor reacted to mass loads similarly to those of the isolated sensors (FIG. 22).

The experiments show an integration of a flexible wishbone-array magnetoelastic sensor and conformal magnetic layer with a biliary stent as a wireless system that may monitor the stent environment. The system was sensitive to physiologically appropriate viscosity changes, showing a 7% decrease in resonant frequency in 10 cP fluid. The system was capable of measuring mass buildup that is associated with sludge accumulation, showing a 38% decrease in the resonant frequency after an applied mass load of 20.9 mg, or 2.3× the mass of the sensor. The integrated system is robust to deformations required for delivery and provides a uniform biasing layer that minimally affects stent mechanics.

With appropriate scaling, the sensing methodology may be applicable in any stent, including cardiovascular and esophageal stents. Additionally, the improved viscosity sensitivity of the wishbone-array sensor may find use in industrial applications like monitoring oil refinement.

Figure 23:
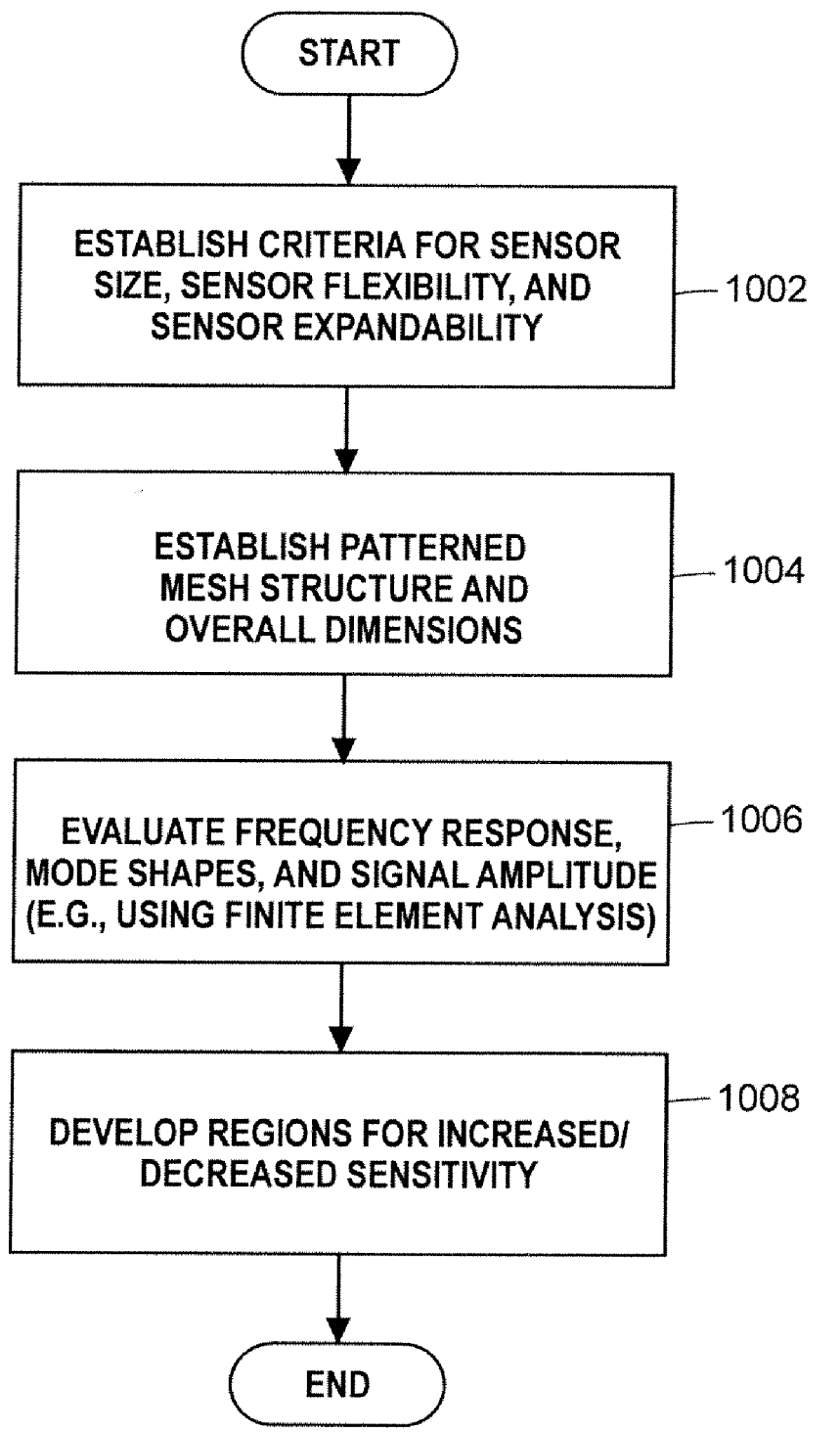
FIG. 23 is a block diagram of an example technique for designing a magnetoelastic sensor.

FIG. 23 provides an example technique 1000 for designing a magnetoelastic sensor such as that discussed with respect to FIG. 6 above. A first block 1002 establishes design criteria for the sensor, e.g., sensor size, flexibility rating, the sensor expandability. Once the design criteria have been set, a block 1004 establishes a pattern mesh structure for the sensor and the overall dimensions of the sensor. In some examples, the mesh structure may be based on the mesh structure of an accompanying stent, which may also be design criteria established by block 1002. Typically, block 1002 will rely on user provided data, while block 1004 is automated, although neither block need be that way. A block 1006 uses a finite element analysis or other technique to evaluate a frequency response, mode shape, and signal amplitude for the magnetoelastic sensor design from block 1004. A block 1008 then modifies the sensor based on the mode shapes to increase or decrease sensitivity at certain locations, such as at anti-nodal points, as discussed herein. The system 1000 may represent a complete computational system producing fabrication data from block 1008 and to be used in fabricating the sensor. In other examples, the blocks 1004 or 1006 may include sensor fabrication to an initial sensor state, while block 1008 would include further manufacturing to form the regions of increased/decreased sensitivity.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

What is claimed is:

1. A magnetoelastic sensor for use in measuring a physical pathology characteristic within an implanted stent, the sensor comprising an elongated body with a patterned structure, formed of a magnetoelastic material, and positioned within the stent such that the sensor will mechanically vibrate under application of a time-varying magnetic field and generate a magnetic flux that has a resonant characteristic that varies with a value of the physical pathology characteristic within the implanted stent, wherein the patterned structure is selectively altered at points to selectively increase or to selectively decrease sensitivity to the physical pathological characteristic at the altered points.

2. The sensor of claim 1, where the patterned structure is configured such that the elongated body has multiple vibration modes that are excited in response to a different frequency of the time-varying magnetic field, where the multiple vibration modes once excited create longitudinal, transverse, and/or bending motion in the sensor.

3. The sensor of claim 1, wherein the patterned structure comprises a wishbone-array pattern.

4. The sensor of claim 3, wherein the physical pathological characteristic results in accumulated mass, changes in stiffness of the sensor or surrounding material, or changes in viscosity of material in the stent, and wherein the patterned structure comprises regions of increased sensitivity at anti-nodal points of the wishbone pattern, wherein the anti-nodal points correspond to locations on the elongated body that experience the largest displacement at the resonant characteristic.

5. The sensor of claim 4, wherein the regions of increased sensitivity comprise an increased surface area of the patterned structure at the anti-nodal points.

6. The sensor of claim 4, wherein the regions of increased sensitivity comprise a selective application of a material coating to the patterned structure.

7. The sensor of claim 4, wherein the regions of increased sensitivity comprise a selective application of surface texture to the patterned structure.

8. The sensor of claim 1, wherein the patterned structure has features extending out of a curvilinear plane of the elongated body to increase or decrease sensitivity and to alter a harmonic response of at least a portion of the sensor.

9. The sensor of claim 1, wherein the patterned structure has a periodic lattice structure, and wherein the periodic lattice structure is selectively altered at points to selectively attract or to selectively repel mass accumulation within the implanted stent.

10. The sensor of claim 1, wherein the resonant characteristic is a resonant frequency, an anti-resonant frequency, a bandwidth between the resonant frequency and the anti-resonant frequency, or a quality factor of either an anti-resonant dip or of a resonant peak, or a combination thereof.

11. The sensor of claim 1, wherein the patterned structure has a plurality of regions along an elongated length that are each of different pattern size or type.

12. The sensor of claim 1, wherein the patterned structure comprises a wishbone-array pattern, a zigzag pattern, a polygonal pattern, a diamond pattern, or a spiral pattern.

13. The sensor of claim 1, wherein the patterned structure has a first region with first mass loading effects and viscosity response and a second region with second, different mass loading effects and viscosity response.

14. The sensor of claim 13, wherein the first region and the second region are mechanically coupled through a flexible coupling.

15. The sensor of claim 1, wherein the patterned structure has different regions of different length, each region coupled to another region by at least one mechanical coupler, and each region having a resonant frequency, where at least two regions have resonant frequencies different from each other.

16. The sensor of claim 15, wherein each region has a different length along a longitudinal axis.

17. The sensor of claim 1, wherein the patterned structure has a first region having a first resonant frequency and a second region having a second resonant frequency.

18. The sensor of claim 17, wherein the patterned structure has a uniform pattern across the first region and the second region, such that the patterned structure is a uniform spatially sensitive structure.

19. The sensor of claim 17, wherein the first region and the second region are mechanically coupled through a flexible coupling, such that applying to the first region a magnetic field oscillating at the first resonant frequency will generate in the second region the magnetic flux at the second resonant frequency through parametric resonance.

20. The sensor of claim 1, wherein the patterned structure has a stimulation region responsive to an external magnetic field and a transmission region to generate the magnetic flux for coupling to an external magnetic sensor.

21. The sensor of claim 1, wherein the patterned structure includes a composition comprising plastic material.

22. The sensor of claim 1, wherein the patterned structure includes a composition comprising a metal material.

23. The sensor of claim 1, wherein the patterned structure includes a composition comprising a rare-earth giant magnetostrictive material.

24. The sensor of claim 1, wherein the patterned structure includes a composition comprising an amorphous metal material.

25. The sensor of claim 1, wherein the sensor has a planar, pre-deployed position and is configured to have a tubular position when deployed.

26. The sensor of claim 1, further comprising spacers for controlling the position of the sensor within the stent.

27. An apparatus comprising:
a stent having a tubular structure when deployed, wherein the stent has a conformal magnetic layer for imparting a biasing magnetic field on a sensor; and
a sensor inserted within the stent and having an elongated body having a patterned structure and formed of a magnetoelastic material to mechanically vibrate under application of a time-varying magnetic field to generate a magnetic flux having a resonant characteristic that varies with a value of a physical pathology characteristic within the implanted stent, wherein the patterned structure is selectively altered at points to selectively increase or to selectively decrease sensitivity to the physical pathological characteristic at the altered points.

28. The apparatus of claim 27, wherein the conformal magnetic layer comprises a polymer coated layer with suspended magnetic particles, a sputtered magnetic layer, or electrodeposited magnetic layer on a surface of the tubular structure.

29. The apparatus of claim 27, wherein the conformal magnetic layer is continuous along an entire length of the stent.

30. The apparatus of claim 27, further comprising spacers for spacing an outer surface of the sensor from an inner surface of the stent.

31. The apparatus of claim 30, wherein the spacers space the sensor from the stent by 100 microns or less.

32. The apparatus of claim 27, further comprising a mechanically decoupling layer on the sensor to attach the sensor to an inner surface of the stent and allow mechanical vibration of the sensor in longitudinal and transverse directions under the application of the time-varying magnetic field.

33. The apparatus of claim 27, wherein the sensor is formed monolithically with the stent in a pre-deployed position.

34. The apparatus of claim 33, further comprising;
at least one connecting beam connecting the stent and the sensor in the pre-deployed position; and
at least one beam joint that is bendable to allow the stent to be repositioned from a pre-deployed position to a deployed position within the stent.

35. The apparatus of claim 27, further comprising an external electromagnetic coil assembly having a transmit coil section to generate the time-varying magnetic field and a receive coil section to receive the magnetic flux having the resonant characteristic that varies with the value of the physical pathology characteristic.

36. The apparatus of claim 35, wherein the transmit coil section and the receive coil section are configured such that the time-varying magnetic field generated by the transmit coil section and coupled to the sensor is not received by the receiver coil section.

37. The apparatus of claim 36, wherein the transmit coil section and the receive coil section are configured such that a longitudinal axis of the receive coil is oriented orthogonally with the direction of the time-varying magnetic field generated by the transmit coil, and such that the longitudinal axis is parallel to the direction of the magnetic flux generated by the sensor.

38. The apparatus of claim 36, wherein the receive coil section is positioned at a null point of the transmit coil section.

39. A method of measuring a physical pathology characteristic within an implantable stent, the method comprising:
disposing a sensor within the stent, the sensor comprising an elongated body having a patterned structure formed of a magnetoelastic material to mechanically vibrate under the application of a magnetic field to generate a magnetic flux having a resonant characteristic that varies with a value of the physical pathology characteristic within the implanted stent;

identifying anti-nodal points of the patterned structure, the anti-nodal points corresponding to points on the patterned structure that experience the largest displacement when the stimulation magnetic field is at a resonant characteristic of the patterned structure;

increasing the sensitivity of the sensor to the physical pathological characteristic at the anti-nodal points of the patterned structure in comparison to other locations on the patterned structure applying an externally generated stimulation magnetic field to at least a first region of the sensor, the stimulation magnetic field being a time-varying magnetic field; and in response to the externally generated stimulation magnetic field and at least at a second region of the sensor, generating a transmitting magnetic field that varies with the value of the physical pathology characteristic.

40. The method of claim 39, further comprising forming the patterned structure of the sensor in a wishbone pattern.

41. The method of claim 39, further comprising increasing the sensitivity at the anti-nodal points by increasing surface area of connection points at the anti-nodal points in comparison to connection points not at the anti-nodal points.

42. The method of claim 39, further comprising texturing the patterned mesh structure at the anti-nodal points.

43. The method of claim 39, further comprising increasing the sensitivity of the patterned structure to the physical pathology characteristic by extending features out of a curvilinear plane of the curved body to increase sensitivity and to alter a frequency response of at least a portion of the sensor.

44. The method of claim 39, further comprising:
applying the stimulation magnetic field at a first resonant frequency of the first region;
parametrically converting vibrational energy generated in the first region to vibrational energy generated in the second region; and
generating the transmitting magnetic field in the second region and at a second resonant frequency that is different than the first resonant frequency.

45. The method of claim 39, further comprising:
applying the stimulation magnetic field to generate a first signal in the first region;
communicating the first signal in the first region to the second region to generate a second signal; and
measuring a time delay or frequency shift between the first signal and the second signal.

46. The method of claim 39, further comprising annealing the sensor to form a 3-D shape for the sensor, the 3-D shape having a curved outer wall complimentary to a curvature of the implantable stent.

47. The method of claim 46, wherein the 3-D shape has features that extend out of a curvilinear plane containing the curved outer wall to transmit compression waves into a surrounding fluid to enhance coupling between the sensor and the surrounding fluid.

48. The method of claim 39, wherein the time-varying magnetic field comprises a pulsed signal, an impulse signal, or a continuous wave signal.

49. The sensor of claim 1, wherein the elongated body comprises a plurality of ribbons extending along a longitudinal axis, adjacent ribbons being mechanically coupled together by couplers configured to transfer mechanical vibrations between adjacent ribbons.

* * * * *